(12) United States Patent
Knutzon

(10) Patent No.: US 6,459,018 B1
(45) Date of Patent: Oct. 1, 2002

(54) POLYUNSATURATED FATTY ACIDS IN PLANTS

(75) Inventor: Debbie Knutzon, Granite Bay, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/330,235

(22) Filed: Jun. 10, 1999

Related U.S. Application Data

(60) Provisional application No. 60/089,043, filed on Jun. 12, 1998.

(51) Int. Cl.$^7$ .......................... A01H 5/00; C12N 15/82
(52) U.S. Cl. ..................... 800/281; 800/298; 435/69.1; 435/419; 435/468
(58) Field of Search ................................ 800/281, 298; 435/468, 419, 69.1

(56) References Cited

U.S. PATENT DOCUMENTS

| | | | |
|---|---|---|---|
| 5,057,419 A | 10/1991 | Martin et al. | |
| 5,376,541 A | 12/1994 | Kawashima et al. | |
| 5,443,974 A | 8/1995 | Hitz et al. | |
| 5,552,306 A | 9/1996 | Thomas et al. | |
| 5,614,393 A | 3/1997 | Thomas et al. | |
| 5,614,400 A | 3/1997 | Cahoon et al. | |
| 5,968,809 A | 10/1999 | Knutzon et al. | |
| 5,972,664 A | 10/1999 | Knutzon et al. | |
| 6,051,754 A | 4/2000 | Knutzon et al. | |
| 6,075,183 A | 6/2000 | Knutzon et al. | |
| 6,136,574 A | 10/2000 | Knutzon et al. | |

FOREIGN PATENT DOCUMENTS

| | | |
|---|---|---|
| EP | 550162 | 7/1993 |
| EP | 561569 | 9/1993 |
| EP | 644263 | 3/1995 |
| EP | 736598 | 1/1996 |
| WO | WO 91/13972 | 9/1991 |
| WO | WO 93/06712 | 4/1993 |
| WO | WO 93/11245 | 6/1993 |
| WO | WO 94/11516 | 5/1994 |
| WO | WO 94/18337 | 8/1994 |
| WO | WO 96/10086 | 4/1996 |
| WO | WO 96/21022 | 7/1996 |
| WO | WO 97/30582 | 8/1997 |

OTHER PUBLICATIONS

Reddy and Thomas, "Expression of a cyanobacterial $\Delta^6$desaturase gene results in gamma–linolenic acid production in transgenic plants," Nature Biotechnology 14:639–642 (May 1996).

"Exciting prospects for stearidonic acid seed oils," Lipid Technology (Nov. 1996).

*Primary Examiner*—Elizabeth F. McElwain
(74) *Attorney, Agent, or Firm*—Sonnenschein Nath & Rosenthal

(57) ABSTRACT

The present invention relates to compositions and methods for preparing polyunsaturated long chain fatty acids in plants, plant parts and plant cells, such as leaves, roots, fruits and seeds. Nucleic acid sequences and constructs encoding fatty acid desaturases, including $\Delta$5-desaturases, $\Delta$6-desaturases and $\Delta$12-desaturases, are used to generate transgenic plants, plant parts and cells which contain and express one or more transgenes encoding one or more desaturases. Expression of the desaturases with different substrate specificities in the plant system permit the large scale production of polyunsaturated long chain fatty acids such as docosahexaenoic acid, eicosapentaenoic acid, α-linolenic acid, gamma-linolenic acid, arachidonic acid and the like for modification of the fatty acid profile of plants, plant parts and tissues. Manipulation of the fatty acid profiles allows for the production of commercial quantities of novel plant oils and products.

12 Claims, 2 Drawing Sheets

SEQUENCE LISTING

<160> NUMBER OF SEQ ID NOS: 22

<210> SEQ ID NO 1
<211> LENGTH: 1391
<212> TYPE: DNA
<213> ORGANISM: Caenorhabditis elegans

<400> SEQUENCE: 1

```
caagtttgag gtatggtcgc tcattcctca gaagggttat ccgccacggc tccggtcacc      60
ggcggagatg ttctggttga tgctcgtgca tctcttgaag aaaaggaggc tccacgtgat     120
gtgaatgcaa acactaaaca ggccaccact gaagagccac gcatccaatt accaactgtg     180
gatgctttcc gtcgtgcaat tccagcacac tgtttcgaaa gagatctcgt taaatcaatc     240
agatatttgg tgcaagactt tgcggcactc acaattctct actttgctct tccagctttt     300
gagtactttg gattgtttgg ttacttggtt tggaacattt tatgggagt ttttggattc      360
gcgttgttcg tcgttggaca cgattgtctt catggatcat tctctgataa tcagaatctc     420
aatgatttca ttggacatat cgccttctca ccactcttct ctccatactt cccatggcag     480
aaaagtcaca agcttcacca tgctttcacc aaccacattg acaaagatca tggacacgtg     540
tggattcagg ataaggattg ggaagcaatg ccatcatgga aagatggtt caatccaatt      600
ccattctctg gatggcttaa atggttccca gtgtacactt tattcggttt ctgtgatgga     660
tctcacttct ggccatactc ttcacttttt gttcgtaact ctgaccgtgt tcaatgtgta     720
atctctggaa tctgttgctg tgtgtgtgca tatattgctc taacaattgc tggatcatat     780
tccaattggt tctggtacta ttgggttcca ctttctttct tcggattgat gctcgtcatt     840
gttacctatt tgcaacatgt cgatgatgtc gctgaggtgt acgaggctga tgaatggagc     900
ttcgtccgtg gacaaaccca aaccatcgat cgttactatg gactcggatt ggacacaacg     960
atgcaccata tcacagacgg acacgttgcc catcacttct tcaacaaaat cccacattac    1020
catctcatcg aagcaaccga aggtgtcaaa aaggtcttgg agccgttgtc cgacacccaa    1080
tacgggtaca aatctcaagt gaactacgat ttctttgccc gtttcctgtg gttcaactac    1140
aagctcgact atctcgttca caagaccgcc ggaatcatgc aattccgaac aactctcgag    1200
gagaaggcaa aggccaagta aaagaatatc ccgtgccgtt ctagagtaca caacaactt     1260
ctgcgttttc accggttttg ctctaattgc aattttcctt tgttctatat atatttttt     1320
gcttttaat tttattctct ctaaaaaact tctactttc agtgcgttga atgcataaag      1380
ccataactct t                                                         1391
```

<210> SEQ ID NO 2
<211> LENGTH: 402
<212> TYPE: PRT
<213> ORGANISM: Caenorhabditis elegans

<400> SEQUENCE: 2

```
Met Val Ala His Ser Ser Glu Gly Leu Ser Ala Thr Ala Pro Val Thr
  1               5                  10                  15

Gly Gly Asp Val Leu Val Asp Ala Arg Ala Ser Leu Glu Glu Lys Glu
```

```
                    20                  25                  30
Ala Pro Arg Asp Val Asn Ala Asn Thr Lys Gln Ala Thr Thr Glu Glu
            35                  40                  45

Pro Arg Ile Gln Leu Pro Thr Val Asp Ala Phe Arg Arg Ala Ile Pro
    50                  55                  60

Ala His Cys Phe Glu Arg Asp Leu Val Lys Ser Ile Arg Tyr Leu Val
65                  70                  75                  80

Gln Asp Phe Ala Ala Leu Thr Ile Leu Tyr Phe Ala Leu Pro Ala Phe
                85                  90                  95

Glu Tyr Phe Gly Leu Phe Gly Tyr Leu Val Trp Asn Ile Phe Met Gly
                100                 105                 110

Val Phe Gly Phe Ala Leu Phe Val Val Gly His Asp Cys Leu His Gly
            115                 120                 125

Ser Phe Ser Asp Asn Gln Asn Leu Asn Asp Phe Ile Gly His Ile Ala
    130                 135                 140

Phe Ser Pro Leu Phe Ser Pro Tyr Phe Pro Trp Gln Lys Ser His Lys
145                 150                 155                 160

Leu His His Ala Phe Thr Asn His Ile Asp Lys Asp His Gly His Val
                165                 170                 175

Trp Ile Gln Asp Lys Asp Trp Glu Ala Met Pro Ser Trp Lys Arg Trp
                180                 185                 190

Phe Asn Pro Ile Pro Phe Ser Gly Trp Leu Lys Trp Phe Pro Val Tyr
            195                 200                 205

Thr Leu Phe Gly Phe Cys Asp Gly Ser His Phe Trp Pro Tyr Ser Ser
    210                 215                 220

Leu Phe Val Arg Asn Ser Asp Arg Val Gln Cys Val Ile Ser Gly Ile
225                 230                 235                 240

Cys Cys Cys Val Cys Ala Tyr Ile Ala Leu Thr Ile Ala Gly Ser Tyr
                245                 250                 255

Ser Asn Trp Phe Trp Tyr Tyr Trp Val Pro Leu Ser Phe Phe Gly Leu
                260                 265                 270

Met Leu Val Ile Val Thr Tyr Leu Gln His Val Asp Asp Val Ala Glu
            275                 280                 285

Val Tyr Glu Ala Asp Glu Trp Ser Phe Val Arg Gly Gln Thr Gln Thr
    290                 295                 300

Ile Asp Arg Tyr Tyr Gly Leu Gly Leu Asp Thr Thr Met His His Ile
305                 310                 315                 320

Thr Asp Gly His Val Ala His His Phe Phe Asn Lys Ile Pro His Tyr
                325                 330                 335

His Leu Ile Glu Ala Thr Glu Gly Val Lys Lys Val Leu Glu Pro Leu
                340                 345                 350

Ser Asp Thr Gln Tyr Gly Tyr Lys Ser Gln Val Asn Tyr Asp Phe Phe
            355                 360                 365

Ala Arg Phe Leu Trp Phe Asn Tyr Lys Leu Asp Tyr Leu Val His Lys
    370                 375                 380

Thr Ala Gly Ile Met Gln Phe Arg Thr Thr Leu Glu Glu Lys Ala Lys
385                 390                 395                 400

Ala Lys

<210> SEQ ID NO 3
<211> LENGTH: 41
<212> TYPE: DNA
<213> ORGANISM: synthetic primer
```

<400> SEQUENCE: 3
cuacuacuac uactgcagac aatggtcgct cattcctcag a                      41

<210> SEQ ID NO 4
<211> LENGTH: 38
<212> TYPE: DNA
<213> ORGANISM: synthetic primer

<400> SEQUENCE: 4
caucaucauc augcggccgc ttacttggcc tttgcctt                          38

<210> SEQ ID NO 5
<211> LENGTH: 32
<212> TYPE: DNA
<213> ORGANISM: synthetic polylinker

<400> SEQUENCE: 5
tcgacctgca ggaagcttgc ggccgcggat cc                                32

<210> SEQ ID NO 6
<211> LENGTH: 32
<212> TYPE: DNA
<213> ORGANISM: synthetic polylinker

<400> SEQUENCE: 6
tcgaggatcc gcggccgcaa gcttcctgca gg                                32

<210> SEQ ID NO 7
<211> LENGTH: 1353
<212> TYPE: DNA
<213> ORGANISM: Brassica napus

<400> SEQUENCE: 7

| | | | | | |
|---|---|---|---|---|---|
| aatccatcaa | acctttattc | accacatttc | actgaaaggc | cacacatcta | gagagagaaa | 60 |
| cttcgtccaa | atctctctct | ccagcgatgg | ttgttgctat | ggaccagcgc | agcaatgtta | 120 |
| acggagattc | cggtgcccgg | aaggaagaag | ggtttgatcc | aagcgcacaa | ccaccgttta | 180 |
| agatcggaga | tataagggcg | gcgattccta | agcattgctg | ggtgaagagt | cctttgagat | 240 |
| ctatgagcta | cgtcaccaga | gacattttcg | ccgtcgcggc | tctggccatg | gccgccgtgt | 300 |
| attttgatag | ctggttcctc | tggccactct | actgggttgc | ccaaggaacc | cttttctggg | 360 |
| ccatcttcgt | tcttggccac | gactgtggac | atgggagttt | ctcagacatt | cctctgctga | 420 |
| acagtgtggt | tggtcacatt | cttcattcat | tcatcctcgt | tccttaccat | ggttggagaa | 480 |
| taagccatcg | gacacaccac | cagaaccatg | gccatgttga | aaacgacgag | tcttgggttc | 540 |
| cgttgccaga | aaagttgtac | aagaacttgc | cccatagtac | tcggatgctc | agatacactg | 600 |
| tccctctgcc | catgctcgct | tacccgatct | atctgtggta | cagaagtcct | ggaaaagaag | 660 |
| ggtcacattt | taacccatac | agtagtttat | ttgctccaag | cgagaggaag | cttattgcaa | 720 |
| cttcaactac | ttgctggtcc | ataatgttgg | ccactcttgt | ttatctatcg | ttcctcgttg | 780 |
| atccagtcac | agttctcaaa | gtctatggcg | ttccttacat | tatctttgtg | atgtggttgg | 840 |
| acgctgtcac | gtacttgcat | catcatggtc | acgatgagaa | gttgccttgg | tacagaggca | 900 |
| aggaatggag | ttatttacgt | ggaggattaa | caactattga | tagagattac | ggaatcttca | 960 |
| acaaacatcca | tcacgacatt | ggaactcacg | tgatccatca | tctttttccca | caaatccctc | 1020 |
| actatcactt | ggtcgatgcc | acgagagcag | ctaaacatgt | gttaggaaga | tactacagag | 1080 |
| agccgaagac | gtcaggagca | ataccgattc | acttggtgga | gagtttggtc | gcaagtatta | 1140 |

```
aaaaagatca ttacgtcagt gacactggtg atattgtctt ctacgagaca gatccagatc   1200
tctacgttta tgcttctgac aaatctaaaa tcaattaact tttcttccta gctctattag   1260
gaataaacac tccttctctt ttacttattt gtttctgcta agtttaaa atgtactcgt    1320 gaaacctttt ttttattaat gtatttacgt tac                                1353
```

<210> SEQ ID NO 8
<211> LENGTH: 383
<212> TYPE: PRT
<213> ORGANISM: Brassica napus

<400> SEQUENCE: 8

```
Met Val Val Ala Met Asp Gln Arg Ser Asn Val Asn Gly Asp Ser Gly
  1               5                  10                  15

Ala Arg Lys Glu Glu Gly Phe Asp Pro Ser Ala Gln Pro Pro Phe Lys
                 20                  25                  30

Ile Gly Asp Ile Arg Ala Ala Ile Pro Lys His Cys Trp Val Lys Ser
             35                  40                  45

Pro Leu Arg Ser Met Ser Tyr Val Thr Arg Asp Ile Phe Ala Val Ala
         50                  55                  60

Ala Leu Ala Met Ala Ala Val Tyr Phe Asp Ser Trp Phe Leu Trp Pro
 65                  70                  75                  80

Leu Tyr Trp Val Ala Gln Gly Thr Leu Phe Trp Ala Ile Phe Val Leu
                 85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
    130                 135                 140

Glu Asn Asp Glu Ser Trp Val Pro Leu Pro Glu Lys Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Ser Leu Phe Ala Pro Ser Glu Arg Lys
        195                 200                 205

Leu Ile Ala Thr Ser Thr Thr Cys Trp Ser Ile Met Leu Ala Thr Leu
    210                 215                 220

Val Tyr Leu Ser Phe Leu Val Asp Pro Val Thr Val Leu Lys Val Tyr
225                 230                 235                 240

Gly Val Pro Tyr Ile Ile Phe Val Met Trp Leu Asp Ala Val Thr Tyr
                245                 250                 255

Leu His His His Gly His Asp Glu Lys Leu Pro Trp Tyr Arg Gly Lys
            260                 265                 270

Glu Trp Ser Tyr Leu Arg Gly Gly Leu Thr Thr Ile Asp Arg Asp Tyr
        275                 280                 285

Gly Ile Phe Asn Asn Ile His His Asp Ile Gly Thr His Val Ile His
    290                 295                 300

His Leu Phe Pro Gln Ile Pro His Tyr His Leu Val Asp Ala Thr Arg
305                 310                 315                 320

Ala Ala Lys His Val Leu Gly Arg Tyr Tyr Arg Glu Pro Lys Thr Ser
                325                 330                 335
```

Gly Ala Ile Pro Ile His Leu Val Glu Ser Leu Val Ala Ser Ile Lys
            340                 345                 350

Lys Asp His Tyr Val Ser Asp Thr Gly Asp Ile Val Phe Tyr Glu Thr
            355                 360                 365

Asp Pro Asp Leu Tyr Val Tyr Ala Ser Asp Lys Ser Lys Ile Asn
            370                 375                 380

<210> SEQ ID NO 9
<211> LENGTH: 40
<212> TYPE: DNA
<213> ORGANISM: synthetic primer

<400> SEQUENCE: 9
cuacuacuac uagagcucag cgauggttgt tgctatggac        40

<210> SEQ ID NO 10
<211> LENGTH: 37
<212> TYPE: DNA
<213> ORGANISM: synthetic primer

<400> SEQUENCE: 10
caucaucauc augaattctt aattgatttt agatttg        37

<210> SEQ ID NO 11
<211> LENGTH: 1482
<212> TYPE: DNA
<213> ORGANISM: Mortierella alpina

<400> SEQUENCE: 11

| | | | | | |
|---|---|---|---|---|---|
| gcttcctcca | gttcatcctc | catttcgcca | cctgcattct | ttacgaccgt | taagcaagat | 60 |
| gggaacggac | caaggaaaaa | ccttcacctg | ggaagagctg | gcggcccata | acaccaagga | 120 |
| cgacctactc | ttggccatcc | gcggcagggt | gtacgatgtc | acaaagttct | tgagccgcca | 180 |
| tcctggtgga | gtggacactc | tcctgctcgg | agctggccga | gatgttactc | cggtctttga | 240 |
| gatgtatcac | gcgtttgggg | ctgcagatgc | cattatgaag | aagtactatg | tcggtacact | 300 |
| ggtctcgaat | gagctgccca | tcttcccgga | gccaacggtg | ttccacaaaa | ccatcaagac | 360 |
| gagagtcgag | ggctacttta | cggatcggaa | cattgatccc | aagaatagac | agagatctg | 420 |
| gggacgatac | gctcttatct | ttggatcctt | gatcgcttcc | tactacgcgc | agctctttgt | 480 |
| gcctttcgtt | gtcgaacgca | catggcttca | gtggtgttt | gcaatcatca | tgggatttgc | 540 |
| gtgcgcacaa | gtcggactca | accctcttca | tgatgcgtct | cacttttcag | tgacccacaa | 600 |
| ccccactgtc | tggaagattc | tgggagccac | gcacgacttt | tcaacggag | catcgtacct | 660 |
| ggtgtggatg | taccaacata | tgctcggcca | tcaccctac | accaacattg | ctggagcaga | 720 |
| tcccgacgtg | tcgacgtctg | agcccgatgt | tcgtcgtatc | aagcccaacc | aaaagtggtt | 780 |
| tgtcaaccac | atcaaccagc | acatgtttgt | tcctttcctg | tacggactgc | tggcgttcaa | 840 |
| ggtgcgcatt | caggacatca | cattttgta | ctttgtcaag | accaatgacg | ctattcgtgt | 900 |
| caatcccatc | tcgacatggc | acactgtgat | gttctggggc | ggcaaggctt | ctttgtctg | 960 |
| gtatcgcctg | attgttcccc | tgcagtatct | gcccctgggc | aaggtgctgc | tcttgttcac | 1020 |
| ggtcgcggac | atggtgtcgt | cttactggct | ggcgctgacc | ttccaggcga | accacgttgt | 1080 |
| tgaggaagtt | cagtggccgt | tgcctgacga | gaacggatc | atccaaaagg | actgggcagc | 1140 |
| tatgcaggtc | gagactacgc | aggattacgc | acacgattcg | cacctctgga | ccagcatcac | 1200 |
| tggcagcttg | aactaccagg | ctgtgcacca | tctgttcccc | aacgtgtcgc | agcaccatta | 1260 |

-continued

```
tcccgatatt ctggccatca tcaagaacac ctgcagcgag tacaaggttc ataccttgt    1320 caaggatacg ttttggcaag catttgcttc acatttggag cacttgcgtg ttcttggact    1380
ccgtcccaag gaagagtaga agaaaaaaag cgccgaatga agtattgccc ccttttctc    1440 caagaatggc aaaaggagat caagtggaca ttctctatga ag                       1482
```

<210> SEQ ID NO 12
<211> LENGTH: 446
<212> TYPE: PRT
<213> ORGANISM: Mortierella alpina

<400> SEQUENCE: 12

```
Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335
```

-continued

```
Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
            355                 360                 365

Asp Tyr Ala His Asp Ser His Leu Trp Thr Ser Ile Thr Gly Ser Leu
            370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
                420                 425                 430

Leu Glu His Leu Arg Val Leu Gly Leu Arg Pro Lys Glu Glu
                435                 440                 445
```

```
<210> SEQ ID NO 13
<211> LENGTH: 39
<212> TYPE: DNA
<213> ORGANISM: synthetic primer

<400> SEQUENCE: 13
cuacuacuac uactcgagca agatgggaac ggaccaagg                          39

<210> SEQ ID NO 14
<211> LENGTH: 39
<212> TYPE: DNA
<213> ORGANISM: synthetic primer

<400> SEQUENCE: 14
caucaucauc auctcgagct actcttcctt gggacggag                          39

<210> SEQ ID NO 15
<211> LENGTH: 47
<212> TYPE: DNA
<213> ORGANISM: synthetic primer

<400> SEQUENCE: 15
cuacuacuac uatctagact cgagaccatg gctgctgctc cagtgtg                 47

<210> SEQ ID NO 16
<211> LENGTH: 40
<212> TYPE: DNA
<213> ORGANISM: synthetic primer

<400> SEQUENCE: 16
caucaucauc auaggcctcg agttactgcg ccttacccat                         40

<210> SEQ ID NO 17
<211> LENGTH: 1617
<212> TYPE: DNA
<213> ORGANISM: Mortierella alpina

<400> SEQUENCE: 17
cgacactcct tccttcttct caccgtcct agtcccttc aaccccctc tttgacaaag      60 acaacaaacc atgctgctg ctcccagtgt gaggacgttt actcgggccg aggttttgaa  120
tgccgaggct ctgaatgagg caagaagga tgccgaggca cccttcttga tgatcatcga  180
caacaaggtg tacgatgtcc gcgagttcgt ccctgatcat cccggtggaa gtgtgattct  240
cacgcacgtt ggcaaggacg gcactgacgt ctttgacact tttcaccccg aggctgcttg  300
```

```
ggagactctt gccaactttt acgttggtga tattgacgag agcgaccgcg atatcaagaa      360
tgatgacttt gcggccgagg tccgcaagct gcgtaccttg ttccagtctc ttggttacta      420
cgattcttcc aaggcatact acgccttcaa ggtctcgttc aacctctgca tctggggttt      480
gtcgacggtc attgtggcca agtgggccga gacctcgacc ctcgccaacg tgctctcggc      540
tgcgcttttg ggtctgttct ggcagcagtg cggatggttg gctcacgact ttttgcatca      600
ccaggtcttc caggaccgtt tctggggtga tcttttcggc gccttcttgg aggtgtctg       660 ccagggcttc tcgtcctcgt ggtggaagga caagcacaac actcaccacg ccgcccccaa      720
cgtccacggc gaggatcccg acattgacac ccaccctctg ttgacctgga gtgagcatgc      780
gttggagatg ttctcggatg tcccagatga ggagctgacc cgcatgtggt cgcgtttcat      840
ggtcctgaac cagacctggt tttacttccc cattctctcg tttgcccgtc tcctggtg         900 cctccagtcc attctctttg tgctgcctaa cggtcaggcc cacaagccct cgggcgcgcg       960
tgtgcccatc tcgttggtcg agcagctgtc gcttgcgatg cactggacct ggtacctcgc      1020
caccatgttc ctgttcatca aggatcccgt caacatgctg gtgtacttt tggtgtcgca      1080 ggcggtgtgc ggaaacttgt tggcgatcgt gttctcgctc aaccacaacg gtatgcctgt      1140
gatctcgaag gaggaggcgg tcgatatgga tttcttcacg aagcagatca tcacgggtcg      1200
tgatgtccac ccgggtctat ttgccaactg gttcacgggt ggattgaact atcagatcga      1260
gcaccacttg ttccccttcga tgcctcgcca caacttttca aagatccagc ctgctgtcga      1320
gaccctgtgc aaaaagtaca atgtccgata ccacaccacc ggtatgatcg agggaactgc      1380
agaggtcttt agccgtctga acgaggtctc caaggctgcc tccaagatgg gtaaggcgca      1440
gtaaaaaaaa aaacaaggac gttttttttc gccagtgcct gtgcctgtgc ctgcttccct      1500
tgtcaagtcg agcgtttctg gaaggatcg ttcagtgcag tatcatcatt ctccttttac       1560
cccccgctca tatctcattc atttctctta ttaaacaact tgttccccc ttcaccg         1617
```

<210> SEQ ID NO 18
<211> LENGTH: 457
<212> TYPE: PRT
<213> ORGANISM: Mortierella alpina

<400> SEQUENCE: 18

```
Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140
```

```
Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
            165                 170                 175

His Gln Val Phe Gln Asp Arg Phe Trp Gly Asp Leu Phe Gly Ala Phe
        180                 185                 190

Leu Gly Gly Val Cys Gln Gly Phe Ser Ser Trp Trp Lys Asp Lys
    195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln
    450                 455

<210> SEQ ID NO 19
<211> LENGTH: 1488
<212> TYPE: DNA
<213> ORGANISM: Mortierella alpina

<400> SEQUENCE: 19
gtcccctgtc gctgtcggca cacccatcc tccctcgctc cctctgcgtt tgtccttggc    60
ccaccgtctc tcctccaccc tccgagacga ctgcaactgt aatcaggaac cgacaaatac   120
acgatttctt tttactcagc accaactcaa aatcctcaac cgcaacccct tttcaggatg   180
gcacctccca acactatcga tgccggtttg acccagcgtc atatcagcac ctcggcccca   240
aactcggcca agcctgcctt cgagcgcaac taccagctcc ccgagttcac catcaaggag   300
```

-continued

```
atccgagagt gcatccctgc ccactgcttt gagcgctccg gtctccgtgg tctctgccac    360
gttgccatcg atctgacttg ggcgtcgctc ttgttcctgg ctgcgaccca gatcgacaag    420
tttgagaatc ccttgatccg ctatttggcc tggcctgttt actggatcat gcagggtatt    480
gtctgcaccg gtgtctgggt gctggctcac gagtgtggtc atcagtcctt ctcgacctcc    540
aagaccctca caacacagt tggttggatc ttgcactcga tgctcttggt ccctaccac    600
tcctggagaa tctcgcactc gaagcaccac aaggccactg ccatatgac aaggaccag    660
gtctttgtgc ccaagacccg ctcccaggtt ggcttgcctc ccaaggagaa cgctgctgct    720
gccgttcagg aggaggacat gtccgtgcac ctggatgagg aggctcccat gtgactttg    780
ttctggatgg tgatccagtt cttgttcgga tggcccgcgt acctgattat gaacgcctct    840
ggccaagact acggccgctg gacctcgcac ttccacacgt actcgcccat ctttgagccc    900
cgcaacttt tcgacattat tatctcggac ctcggtgtgt tggctgccct cggtgccctg    960
atctatgcct ccatgcagtt gtcgctcttg accgtcacca agtactatat tgtcccctac   1020
ctctttgtca actttggtt ggtcctgatc accttcttgc agcacaccga tcccaagctg   1080
ccccattacc gcgagggtgc ctggaatttc agcgtggag ctctttgcac cgttgaccgc   1140
tcgtttggca agttcttgga ccatatgttc acggcattg tccacaccca tgtggcccat   1200
cacttgttct cgcaaatgcc gttctaccat gctgaggaag ctacctatca tctcaagaaa   1260
ctgctgggag agtactatgt gtacgaccca tccccgatcg tcgttgcggt ctggaggtcg   1320
ttccgtgagt gccgattcgt ggaggatcag ggagacgtgg tcttttttcaa gaagtaaaaa   1380
aaaagacaat ggaccacaca caaccttgtc tctacagacc tacgtatcat gtagccatac   1440
cacttcataa aagaacatga gctctagagg cgtgtcattc gcgcctcc                 1488
```

<210> SEQ ID NO 20
<211> LENGTH: 399
<212> TYPE: PRT
<213> ORGANISM: Mortierella alpina

<400> SEQUENCE: 20

```
Met Ala Pro Pro Asn Thr Ile Asp Ala Gly Leu Thr Gln Arg His Ile
1               5                   10                  15

Ser Thr Ser Ala Pro Asn Ser Ala Lys Pro Ala Phe Glu Arg Asn Tyr
            20                  25                  30

Gln Leu Pro Glu Phe Thr Ile Lys Glu Ile Arg Glu Cys Ile Pro Ala
        35                  40                  45

His Cys Phe Glu Arg Ser Gly Leu Arg Gly Leu Cys His Val Ala Ile
    50                  55                  60

Asp Leu Thr Trp Ala Ser Leu Leu Phe Leu Ala Ala Thr Gln Ile Asp
65                  70                  75                  80

Lys Phe Glu Asn Pro Leu Ile Arg Tyr Leu Ala Trp Pro Val Tyr Trp
                85                  90                  95

Ile Met Gln Gly Ile Val Cys Thr Gly Val Trp Val Leu Ala His Glu
            100                 105                 110

Cys Gly His Gln Ser Phe Ser Thr Ser Lys Thr Leu Asn Asn Thr Val
        115                 120                 125

Gly Trp Ile Leu His Ser Met Leu Leu Val Pro Tyr His Ser Trp Arg
    130                 135                 140

Ile Ser His Ser Lys His His Lys Ala Thr Gly His Met Thr Lys Asp
145                 150                 155                 160

Gln Val Phe Val Pro Lys Thr Arg Ser Gln Val Gly Leu Pro Pro Lys
```

-continued 165                 170                 175

Glu Asn Ala Ala Ala Val Gln Glu Glu Asp Met Ser Val His Leu
                180             185             190

Asp Glu Glu Ala Pro Ile Val Thr Leu Phe Trp Met Val Ile Gln Phe
            195                 200             205

Leu Phe Gly Trp Pro Ala Tyr Leu Ile Met Asn Ala Ser Gly Gln Asp
        210                 215             220

Tyr Gly Arg Trp Thr Ser His Phe His Thr Tyr Ser Pro Ile Phe Glu
225                 230             235                 240

Pro Arg Asn Phe Phe Asp Ile Ile Ile Ser Asp Leu Gly Val Leu Ala
                245             250             255

Ala Leu Gly Ala Leu Ile Tyr Ala Ser Met Gln Leu Ser Leu Leu Thr
                260             265             270

Val Thr Lys Tyr Tyr Ile Val Pro Tyr Leu Phe Val Asn Phe Trp Leu
            275             280             285

Val Leu Ile Thr Phe Leu Gln His Thr Asp Pro Lys Leu Pro His Tyr
        290             295             300

Arg Glu Gly Ala Trp Asn Phe Gln Arg Gly Ala Leu Cys Thr Val Asp
305             310             315                 320

Arg Ser Phe Gly Lys Phe Leu Asp His Met Phe His Gly Ile Val His
                325             330             335

Thr His Val Ala His His Leu Phe Ser Gln Met Pro Phe Tyr His Ala
                340             345             350

Glu Glu Ala Thr Tyr His Leu Lys Lys Leu Leu Gly Glu Tyr Tyr Val
            355             360             365

Tyr Asp Pro Ser Pro Ile Val Val Ala Val Trp Arg Ser Phe Arg Glu
        370             375             380

Cys Arg Phe Val Glu Asp Gln Gly Asp Val Val Phe Phe Lys Lys
385             390             395

<210> SEQ ID NO 21
<211> LENGTH: 36
<212> TYPE: DNA
<213> ORGANISM: synthetic primer

<400> SEQUENCE: 21
cuacuacuac uaggatccat ggcacctccc aacact                                       36

<210> SEQ ID NO 22
<211> LENGTH: 41
<212> TYPE: DNA
<213> ORGANISM: synthetic primer

<400> SEQUENCE: 22
caucaucauc auggtacctc gagttacttc ttgaaaaaga c                                 41

POLYUNSATURATED FATTY ACIDS IN PLANTS

This application claims the benefit of U.S. Provisional Application No. 60/089,043 filed Jun. 12, 1998.

TENHNICAL FIELD

This invention relates to modulating levels of enzymes and/or enzyme components capable of altering the production of long chain polyunsaturated fatty acids (PUFAS) in a host plant. The invention is exemplified by the production of PUFAS in plants.

BACKGROUND

Three main families of polyunsaturated fatty acids (PUFAs) are the 3 fatty acids, exemplified by arachidonic acid, the ω9 fatty acids exemplified by Mead acid, and the ω3 fatty acids, exemplified by eicosapentaenoic acid. PUFAs are important components of the plasma membrane of the cell, where they may be found in such forms as phospholipids. PUFAs also serve as precursors to other molecules of importance in human beings and animals, including the prostacyclins, leukotrienes and prostaglandins. PUFAs are necessary for proper development, particularly in the developing infant brain, and for tissue formation and repair.

Four major long chain PUFAs of importance include docosahexaenoic acid (DHA) and eicosapentaenoic acid (EPA), which are primarily found in different types of fish oil, gamma-linolenic acid (GLA), which is found in the seeds of a number of plants, including evening primrose (*Oenothera biennis*), borage (*Borago officinalis*) and black currants (*Ribes nigrum*), and stearidonic acid (SDA), which is found in marine oils and plant seeds. Both GLA and another important long chain PUFA, arachidonic acid (ARA), are found in filamentous fungi. ARA can be purified from animal tissues including liver and adrenal gland. Mead acid accumulates in essential fatty acid deficient animals.

For DHA, a number of sources exist for commercial production including a variety of marine organisms, oils obtained from cold water marine fish, and egg yolk fractions. For ARA, microorganisms including the genera Mortierella, Entomophthora, Phytium and Porphyridium can be used for commercial production. Commercial sources of SDA include the genera Trichodesma and Echium. Commercial sources of GLA include evening primrose, black currants and borage. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFA. Natural sources also are subject to uncontrollable fluctuations in availability. Fish stocks may undergo natural variation or may be depleted by overfishing. Fish oils have unpleasant tastes and odors, which may be impossible to economically separate from the desired product, and can render such products unacceptable as food supplements. Animal oils, and particularly fish oils, can accumulate environmental pollutants. Weather and disease can cause fluctuation in yields from both fish and plant sources. Cropland available for production of alternate oil-producing crops is subject to competition from the steady expansion of human populations and the associated increased need for food production on the remaining arable land. Crops which do produce PUFAs, such as borage, have not been adapted to commercial growth and may not perform well in monoculture. Growth of such crops is thus not economically competitive where more profitable and better established crops can be grown. Large scale fermentation of organisms such as Mortierella is also expensive. Natural animal tissues contain low amounts of ARA and are difficult to process. Microorganisms such as Porphyridium and Mortierella are difficult to cultivate on a commercial scale.

Dietary supplements and pharmaceutical formulations containing PUFAs can retain the disadvantages of the PUFA source. Supplements such as fish oil capsules can contain low levels of the particular desired component and thus require large dosages. High dosages result in ingestion of high levels of undesired components, including contaminants. Care must be taken in providing fatty acid supplements, as overaddition may result in suppression of endogenous biosynthetic pathways and lead to competition with other necessary fatty acids in various lipid fractions in vivo, leading to undesirable results. For example, Eskimos having a diet high in ω3 fatty acids have an increased tendency to bleed (U.S. Pat. No. 4,874,603). Unpleasant tastes and odors of the supplements can make such regimens undesirable, and may inhibit compliance by the patient.

A number of enzymes are involved in PUFA biosynthesis. Linoleic acid (LA, 18:2 Δ9, 12) is produced from oleic acid (18:1 Δ9) by a Δ12-desaturase. GLA (18:3 Δ6, 9, 12) is produced from linoleic acid (LA, 18:2 Δ9, 12) by a Δ6-desaturase. ARA (20:4 Δ5, 8, 11, 14) production from DGLA (20:3 Δ8, 11, 14) is catalyzed by a Δ5-desaturase. However, animals cannot desaturate beyond the Δ9 position and therefore cannot convert oleic acid (18:1 Δ9) into linoleic acid (18:2 Δ9, 12). Likewise, α-linolenic acid (ALA, 18:3 Δ9, 12, 15) cannot be synthesized by mammals. Other eukaryotes, including fungi and plants, have enzymes which desaturate at positions Δ12 and Δ15. The major poly-unsaturated fatty acids of animals therefore are either derived from diet and/or from desaturation and elongation of linoleic acid (18:2 Δ9, 12) or -linolenic acid (18:3 Δ9, 12, 15).

Poly-unsaturated fatty acids are considered to be useful for nutritional, pharmaceutical, industrial, and other purposes. An expansive supply of poly-unsaturated fatty acids from natural sources and from chemical synthesis are not sufficient for commercial needs. Therefore it is of interest to obtain genetic material involved in PUFA biosynthesis from species that naturally produce these fatty acids and to express the isolated material alone or in combination in a heterologous system which can be manipulated to allow production of commercial quantities of PUFAS.

SUMMARY OF THE INVENTION

Novel compositions and methods are provided for preparation of poly-unsaturated long chain fatty acids and desaturases in plants and plant cells. The methods involve growing a host plant cell of interest transformed with an expression cassette functional in a host plant cell, the expression cassette comprising a transcriptional and translational initiation regulatory region, joined in reading frame 5' to a DNA sequence encoding a desaturase polypeptide capable of modulating the production of PUFAs. Expression of the desaturase polypeptide provides for an alteration in the PUFA profile of host plant cells as a result of altered concentrations of enzymes involved in PUFA biosynthesis. Of particular interest is the selective control of PUFA production in plant tissues and/or plant parts such as leaves, roots, fruits and seeds. The invention finds use for example in the large scale production of DHA, Mead Acid, EPA, ARA, DGLA, stearidonic acid GLA and other fatty acids and for modification of the fatty acid profile of edible plant tissues and/or plant parts.

DESCRIPTION OF THE PREFERRED EMBODIMENTS

Figure 1:
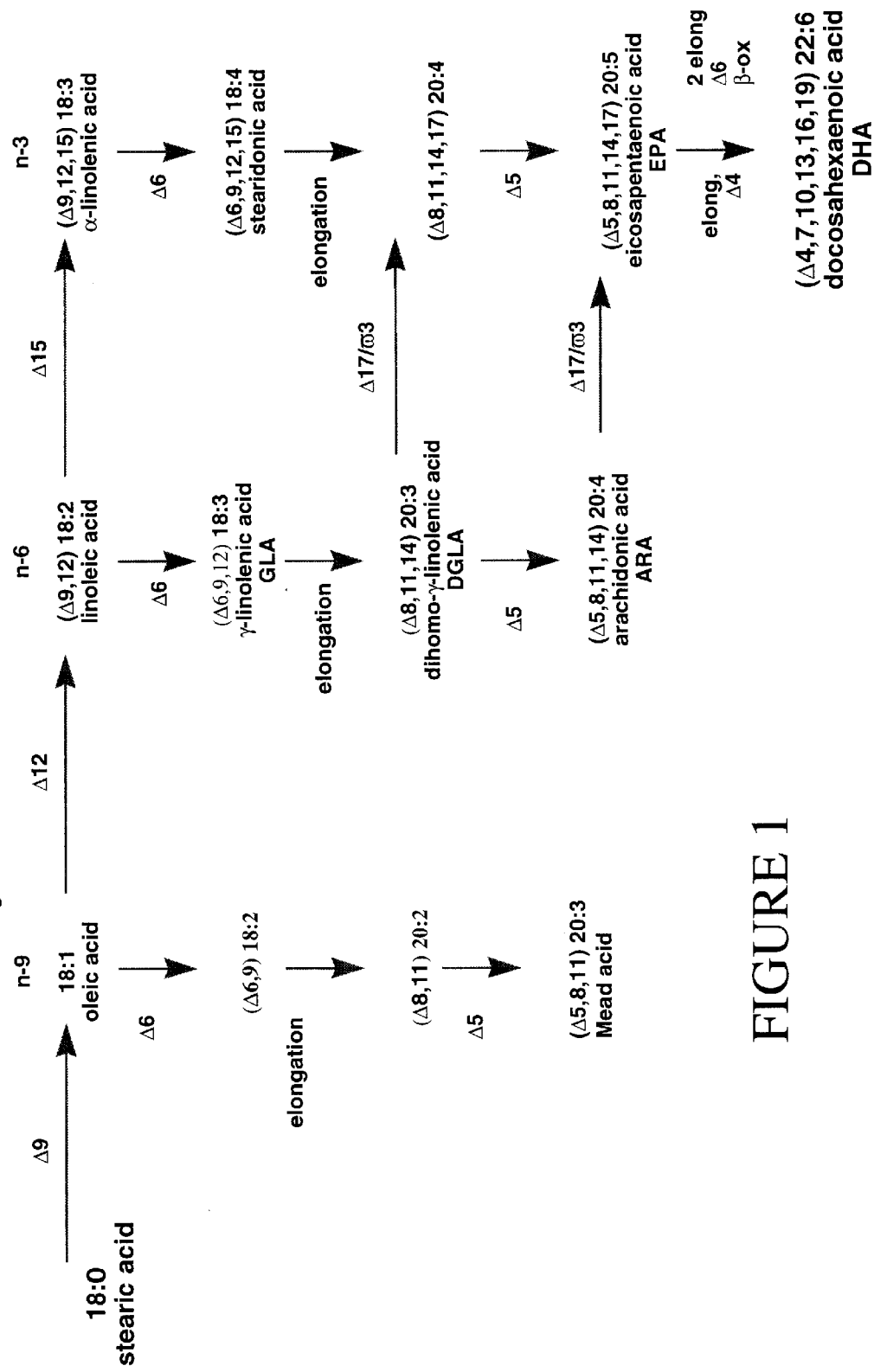
FIG. 1 shows possible pathways for the synthesis of Mead acid (20:3 Δ5, 8, 11), arachidonic acid (20:4 Δ5, 8, 11, 14) and stearidonic acid (18:4 Δ6, 9, 12, 15) from palmitic acid ($C_{16}$) from a variety of organisms, including algae, Mortierella and humans. These PUFAs can serve as precursors to other molecules important for humans and other animals, including prostacyclins, leukotrienes, and prostaglandins, some of which are shown.

In order to ensure a complete understanding of the invention, the following definitions are provided:

Δ5-Desaturase: Δ5 desaturase is an enzyme which introduces a double bond between carbons 5 and 6 from the carboxyl end of a fatty acid molecule.

Δ6-Desaturase: Δ6-desaturase is an enzyme which introduces a double bond between carbons 6 and 7 from the carboxyl end of a fatty acid molecule.

Δ9-Desaturase: Δ9-desaturase is an enzyme which introduces a double bond between carbons 9 and 10 from the carboxyl end of a fatty acid molecule.

Δ12-Desaturase: Δ12-desaturase is an enzyme which introduces a double bond between carbons 12 and 13 from the carboxyl end of a fatty acid molecule.

Fatty acids: Fatty acids are a class of compounds containing a long-hydrocarbon chain and a terminal carboxylate group. Fatty acids include the following:

| Fatty Acid | | |
|---|---|---|
| 12:0 | lauric acid | |
| 16:0 | Palmitic acid | |
| 16:1 | Palmitoleic acid | |
| 18:0 | stearic acid | |
| 18:1 | oleic acid | Δ9–18:1 |
| 18:2 Δ5,9 | Taxoleic acid | Δ5,9–18:2 |
| 18:2 Δ6,9 | 6,9-octadecadienoic acid | Δ6,9–18:2 |
| 18:2 | Linoleic acid | Δ9,12–18:2 (LA) |
| 18:3 Δ6,9,12 | Gamma-linolenic acid | Δ6,9,12–18:3 (GLA) |
| 18:3 Δ5,9,12 | Pinolenic acid | Δ5,9,12–18:3 |
| 18:3 | alpha-linolenic acid | Δ9,12,15–18:3 (ALA) |
| 18:4 | Stearidonic acid | Δ6,9,12,15–18:4 (SDA) |
| 20:0 | Arachidic acid | |
| 20:1 | Eicoscenic Acid | |
| 20:2 Δ8,11 | | Δ8, 11 |
| 20:3 Δ5,8,11 | Mead Acid | Δ5, 8, 11 |
| 22:0 | Behenoic acid | |
| 22:1 | erucic acid | |
| 22:2 | Docasadienoic acid | |
| 20:4 γ6 | Arachidonic acid | Δ5,8,11,14–20:4 (ARA) |
| 20:3 γ6 | γ6-eicosatrienoic dihomo-gamma linolenic | Δ8,11,14–20:3 (DGLA) |
| 20:5 γ3 | Eicosapentaenoic (Timnodonic acid) | Δ5,8,11,14,17–20:5 (EPA) |
| 20:3 γ3 | γ3-eicosatnenoic | Δ11,16,17–20:3 |
| 20:4 γ3 | γ3-eicosatetraenoic | Δ8,11,14,17–20:4 |
| 22:5 γ3 | Docosapentaenoic | Δ7,10,13,16,19–22:5 (γ3DPA) |
| 22:6 γ3 | Docosahexaenoic (cervonic acid) | Δ4,7,10,13,16,19–22:6 (DHA) |
| 24:0 | Lignoceric acid | |

Taking into account these definitions, the present invention is directed to novel DNA sequences, and DNA constructs related to the production of fatty acids in plants. Methods and compositions are provided which permit modification of the poly-unsaturated long chain fatty acid content of plant cells. Plant cells are transformed with an expression cassette comprising a DNA encoding a polypeptide capable of increasing the amount of one or more PUFA in a plant cell. Desirably, integration constructs may be prepared which provide for integration of the expression cassette into the genome of a host cell. Host cells are manipulated to express a sense or antisense DNA encoding a polypeptide(s) that has desaturase activity. By "desaturase" is intended a polypeptide which can desaturate one or more fatty acids to produce a mono- or poly-unsaturated fatty acid or precursor thereof of interest. By "polypeptide" is meant any chain of amino acids, regardless of length or post-translational modification, for example, glycosylation or phosphorylation. The substrate(s) for the expressed enzyme may be produced by the host cell or may be exogenously supplied.

To achieve expression in a host cell, the transformed DNA is operably associated with transcriptional and translational initiation and termination regulatory regions that are functional in the host cell. Constructs comprising the gene to be expressed can provide for integration into the genome of the host cell or can autonomously replicate in the host cell. For production of taxoleic acid, the expression cassettes generally used include a cassette which provides for Δ5 desaturase activity, particularly in a host cell which produces or can take up oleic acid. For production of Δ6,9 18:2 or other ω9 unsaturated fatty acids, the expression cassettes generally used include a cassette which provides for Δ6 desaturase activity, particularly in a host cell which produces or can take up oleic acid. Production of oleic acid, taxoleic acid, or ω9 unsaturated fatty acids in a plant having Δ12 desaturase activity is favored by providing an expression cassette. for an antisense Δ12 transcript, or by disrupting a Δ12 desaturase gene. For production of linoleic acid (LA), the expression cassettes generally used include a cassette which provides for Δ12 desaturase activity, particularly in a host cell which produces or can take up oleic acid. For production of ALA, the expression cassettes generally used include a cassette which provides for Δ15 or ω3 desaturase activity, particularly in a host cell which produces or can take up LA. For production of GLA or SDA, the expression cassettes generally used include a cassette which provides for Δ6 desaturase activity, particularly in a host cell which produces or can take up LA or ALA, respectively. Production of ω6-type unsaturated fatty acids, such as LA or GLA, in a plant capable of producing ALA is favored by inhibiting the activity of Δ15 or ω3 type desaturase; this is accomplished by providing and expression cassette for an antisense Δ15 or ω3 transcript, or by disrupting a Δ15 or ω3 desaturase gene. Similarly, production of LA or ALA in a plant having Δ6 desaturase activity is favored by providing an expression cassette for an antisense A 6 transcript, or by disrupting a Δ6 desaturase gene. For production of ARA in a host cell which produces or can take up DGLA, the expression cassette generally used provides for D5 desaturase activity. Production of ω6-type unsaturated fatty acids, such as ARA, in a plant capable of producing ALA is favored by inhibiting the activity of a Δ15 or ω-3 type desaturase; this is accomplished by providing an expression cassette for an antisense Δ15 or ω3 transcript, or by disrupting a Δ15 of ω3 desaturase gene.

TRANSGENIC PLANT PRODUCTION OF FATTY ACIDS

Transgenic plant production of PUFAs offers several advantages over purification from natural sources such as fish or plants. Production of fatty acids from recombinant plants provides the ability to alter the naturally occurring plant fatty acid profile by providing new synthetic pathways in the host or by suppressing undesired pathways, thereby increasing levels of desired PUFAs, or conjugated forms thereof, and decreasing levels of undesired PUFAs. Production of fatty acids in transgenic plants also offers the advantage that expression of desaturase genes in particular tissues and/or plant parts means that greatly increased levels of desired PUFAs in those tissues and/or parts can be achieved, making recovery from those tissues more economical. For example, the desired PUFAs can be expressed in seed; methods of isolating seed oils are well established. In addition to providing a source for purification of desired PUFAs, seed oil components can be manipulated through expression of desaturase genes, either alone or in combination with other genes such as elongases, to provide seed oils having a particular PUFA profile in concentrated form. The concentrated seed oils then can be added to animal milks and/or synthetic or semi-synthetic milks to serve as infant formulas where human nursing is impossible or undesired, or in cases of malnourishment or disease in both adults and infants.

Figure 2:
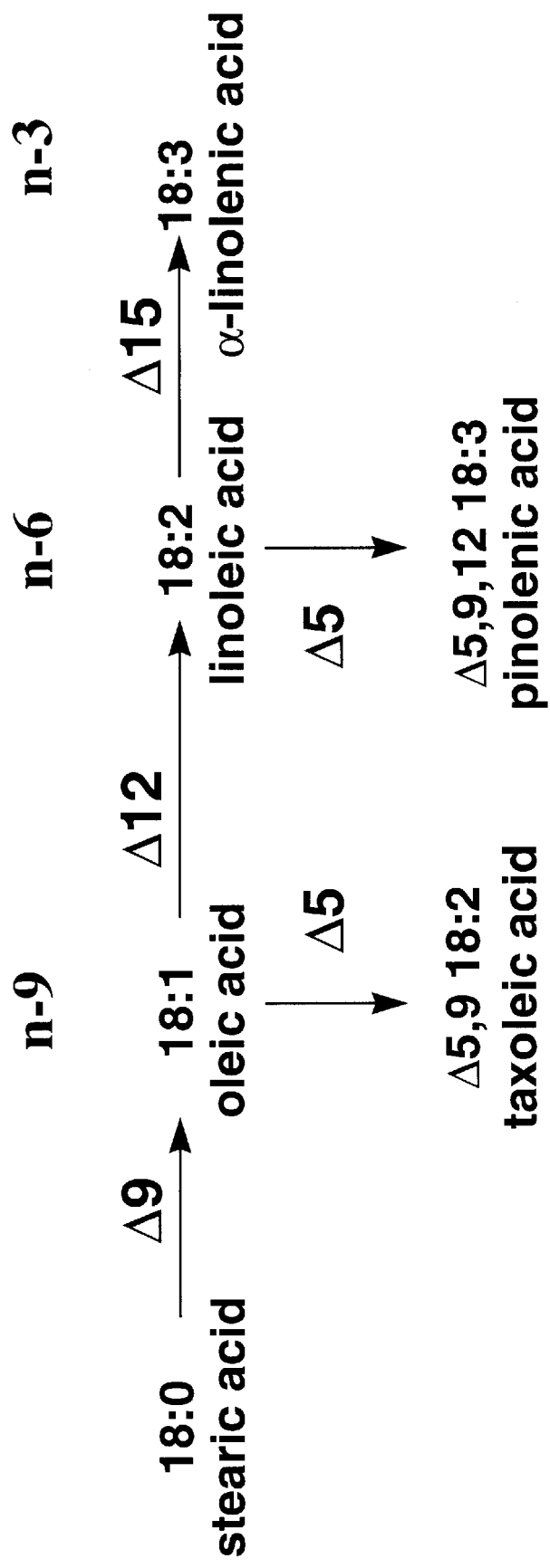
FIG. 2 shows possible pathways for production of PUFAs in addition to ARA, including taxoleic acid and pinolenic, again compiled from a variety of organisms.

For production of PUFAs, depending upon the host cell, the availability of substrate, and the desired end product(s), several polypeptides, particularly desaturases, are of interest including those polypeptides which catalyze the conversion of stearic acid to oleic acid, LA to GLA, of ALA to SDA, of oleic acid to LA, or of LA to ALA, oleic acid to taxolic acid, LA to pinolenic acid, oleic acid to 6,9-actadeca-dienoic acid which includes enzymes which desaturate at the Δ6, Δ9, Δ5, Δ12, Δ15, Δ5, or ω3 positions. Considerations for choosing a specific polypeptide having desaturase activity include the pH optimum of the polypeptide, whether the polypeptide is a rate limiting enzyme or a component thereof, whether the desaturase used is essential for synthesis of a desired poly-unsaturated fatty acid, and/or co-factors required by the polypeptide. The expressed polypeptide preferably has parameters compatible with the biochemical environment of its location in the host cell. For example, the polypeptide may have to compete for substrate with other enzymes in the host cell. Analyses of the $K_m$ and specific activity of the polypeptide in question therefore are considered in determining the suitability of a given polypeptide for modifying PUFA production in a given host cell. The polypeptide used in a particular situation therefore is one which can function under the conditions present in the intended host cell but otherwise can be any polypeptide having desaturase activity which has the desired characteristic of being capable of modifying the relative production of a desired PUFA. A scheme for the synthesis of arachidonic acid (20:4 Δ5, 8, 11, 14) from palmitic acid ($C_{16}$) is shown in FIG. 1. A key enzyme in this pathway is a Δ5-desaturase which converts DH-γ-linolenic acid (DGLA, eicosatrienoic acid) to ARA. Conversion of α-linolenic acid (ALA) to stearidonic acid by a Δ6-desaturase is also shown. Production of PUFAs in addition to ARA, including EPA and DHA is shown in FIG. 2. A key enzyme in the synthesis of arachidonic acid (20:4 Δ5, 8, 11, 14) from stearic acid ($C_{18}$) is a Δ6-desaturase which converts the linoleic acid into γ-linolenic acid. Conversion of α-linolenic acid (ALA) to stearidonic acid by a Δ6-desaturase also is shown. For production of ARA, the DNA sequence used encodes a polypeptide having Δ5 desaturase activity. In particular instances, this can be coupled with an expression cassette which provides for production of a polypeptide having Δ6 desaturase activity and, optionally, a transcription cassette providing for production of antisense sequences to a Δ15 transcription product. The choice of combination of cassettes used depends in part on the PUFA profile of the host cell. Where the host cell Δ5-desaturase activity is limiting, overexpression of Δ5 desaturase alone generally will be sufficient to provide for enhanced ARA production.

SOURCES OF POLYPEPTIDES HAVING DESATURASE ACTIVITY

As sources of polypeptides having desaturase activity and oligonucleotides encoding such polypeptides are organisms which produce a desired poly-unsaturated fatty acid. As an example, microorganisms having an ability to produce ARA can be used as a source of Δ5-desaturase genes; microorganisms which GLA or SDA can be used as a source of Δ6-desaturase and/or Δ12-desaturase genes. Such microorganisms include, for example, those belonging to the genera Mortierella, Conidiobolus, Pythium, Phytophathora, Penicillium, Porphyridium, Coidosporium, Mucor, Fusarium, Aspergillus, Rhodotorula, and Entomophthora. Within the genus Porphyridium, of particular interest is *Porphyridium cruentum*. Within the genus Mortierella, of particular interest are *Mortierella elongata, Mortierella exigua, Mortierella hygrophila, Mortierella ramanniana*, var. *angulispora*, and *Mortierella alpina*. Within the genus Mucor, of particular interest are *Mucor circinelloides* and *Mucor javanicus*.

DNAs encoding desired desaturases can be identified in a variety of ways. As an example, a source of the desired desaturase, for example genomic or cDNA libraries from Mortierella, is screened with detectable enzymatically- or chemically-synthesized probes, which can be made from DNA, RNA, or non-naturally occurring nucleotides, or mixtures thereof. Probes may be enzymatically synthesized from DNAs of known desaturases for normal or reduced-stringency hybridization methods. Oligonucleotide probes also can be used to screen sources and can be based on sequences of known desaturases, including sequences conserved among known desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR from reverse transcribed mRNA from a known or suspected source; the PCR product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA can also be employed.

For the most part, some or all of the coding sequence for the polypeptide having desaturase activity is from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having desaturase activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally occurring desaturase genes to produce a polypeptide having desaturase activity in vivo with more desirable physical and kinetic parameters for function in the host cell, such as a longer half-life or a higher rate of production of a desired polyunsaturated fatty acid.

Desirable cDNAs have less than 60% A+T composition, preferably less than 50% A+T composition. On a localized scale of a sliding window of 20 base pairs, it is preferable that there are no localized regions of the cDNA with greater than 75% A+T composition; with a window of 60 base pairs, it is preferable that there are no localized regions of the cDNA with greater than 60%, more preferably no localized regions with greater than 55% A+T composition.

Mortierella Alpina Desaturases

Of particular interest are the *Mortierella alpina* Δ5-desaturase, Δ6-desaturase, Δ12-desaturase and Δ15 desaturase. The gene encoding the *Mortierella alpina* Δ5-desaturase can be expressed in transgenic plants to effect greater synthesis of ARA from DGLA, or pinolenic acid from LA, taxoleic acid from oleic acid or Mead and from Δ8, 11-20:2. Other DNAs which are substantially identical in sequence to the *Mortierella alpina* Δ5-desaturase DNA, or which encode polypeptides which are substantially identical in sequence to the *Mortierella alpina*Δ5-desaturase polypeptide, also can be used. The gene encoding the *Mortierella alpina* Δ6-desaturase can be expressed in transgenic plants or animals to effect greater synthesis of GLA from linoleic acid or of stearidonic acid (SDA) from ALA or of 6,9-octadecadienoic acid from oleic acid. Other DNAs which are substantially identical in sequence to the *Mortierella alpina* Δ6-desaturase DNA, or which encode polypeptides which are substantially identical in sequence to the *Mortierella alpina* Δ6-desaturase polypeptide, also can be used.

The gene encoding the *Mortierella alpina* Δ12-desaturase can be expressed in transgenic plants to effect greater synthesis of LA from oleic acid. Other DNAs which are substantially identical to the *Mortierella alpina* Δ12-desaturase DNA, or which encode polypeptides which are substantially identical to the *Mortierella alpina* Δ12-desaturase polypeptide, also can be used.

By substantially identical in sequence is intended an amino acid sequence or nucleic acid sequence exhibiting in order of increasing preference at least 60%, 80%, 90% or 95% homology to the *Mortierella alpina* Δ5-desaturase amino acid sequence or nucleic acid sequence encoding the amino acid sequence. For polypeptides, the length of comparison sequences generally is at least 16 amino acids, preferably at least 20 amino acids, or most preferably 35 amino acids. For nucleic acids, the length of comparison sequences generally is at least 50 nucleotides, preferably at least 60 nucleotides, and more preferably at least 75 nucleotides, and most preferably, 110 nucleotides. Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* 157: 105–132, 1982), or on the basis of the ability to assume similar polypeptide secondary structure (Chou and Fasman, *Adv. Enzymol.* 47: 45–148, 1978).

EXPRESSION OF DESATURASE GENES

Once the DNA encoding a desaturase polypeptide has been obtained, it is placed in a vector capable of replication in a host cell, or is propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell.

For expression of a desaturase polypeptide, functional transcriptional and translational initiation and termination regions are operably linked to the DNA encoding the desaturase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is easily harvested, such as seed, leaves, fruits, flowers, roots, etc. Expression can be targeted to that location within the plant by using specific regulatory sequences, such as those of U.S. Pat. No. 5,463,174, U.S. Pat. No. 4,943,674, U.S. Pat. No. 5,106,739, U.S. Pat. No. 5,175,095, U.S. Pat. No. 5,420,034, U.S. Pat. No. 5,188,958, and U.S. Pat. No. 5,589,379.

Alternatively, the expressed protein can be an enzyme which produces a product which may be incorporated, either directly or upon further modifications, into a fluid fraction from the host plant. In the present case, expression of desaturase genes, or antisense desaturase transcripts, can alter the levels of specific PUFAs, or derivatives thereof, found in plant parts and/or plant tissues. The $\Delta 5$-desaturase polypeptide coding region is expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property.

The choice of a host cell is influenced in part by the desired PUFA profile of the transgenic cell, and the native profile of the host cell. As an example, for production of linoleic acid from oleic acid, the DNA sequence used encodes a polypeptide having $\Delta 12$ desaturase activity, and for production of GLA from linoleic acid, the DNA sequence used encodes a polypeptide having $\Delta 6$ desaturase activity. Use of a host cell which expresses $\Delta 12$ desaturase activity and lacks or is depleted in $\Delta 15$ desaturase activity, can be used with an expression cassette which provides for over-expression of $\Delta 6$ desaturase alone generally is sufficient to provide for enhanced GLA production in the transgenic cell. Where the host cell expresses $\Delta 9$ desaturase activity, expression of both a $\Delta 12$- and a $\Delta 6$-desaturase can provide for enhanced GLA production. In particular instances where expression of $\Delta 6$ desaturase activity is coupled with expression of $\Delta 12$ desaturase activity, it is desirable that the host cell naturally have, or be mutated to have, low $\Delta 15$ desaturase activity. Alternatively, a host cell for $\Delta 6$ desaturase expression may have, or be mutated to have, high $\Delta 12$ desaturase activity.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the desaturase polypeptide in the source plant is desired, several methods can be employed. Additional genes encoding the desaturase polypeptide can be introduced into the host organism. Expression from the native desaturase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (see U.S. Pat. No. 4,910,141 and U.S. Pat. No. 5,500,365.)

When it is desirable to express more than one different gene, appropriate regulatory regions and expression methods, introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

Constructs comprising the gene of interest may be introduced into a host cell by standard techniques. These techniques include transfection, infection, bolistic impact, electroporation, microinjection, scraping, or any other method which introduces the gene of interest into the host cell (see U.S. Pat. No. 4,743,548, U.S. Pat. No. 4,795,855, U.S. Pat. No. 5,068,193, U.S. Pat. No. 5,188,958, U.S. Pat. No. 5,463,174, U.S. Pat. No. 5,565,346 and U.S. Pat. No. 5,565,347). For convenience, a host cell which has been manipulated by any method to take up a DNA sequence or construct will be referred to as "transformed" or "recombinant" herein. The subject host will have at least have one copy of the expression construct and may have two or more, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host cell. Desirably, resistance to kanamycin and the amino glycoside G418 are of interest (see U.S. Pat. No. 5,034,322). Selection of a transformed host can also occur when the expressed marker protein can be detected, either directly or indirectly. The marker protein may be expressed alone or as a fusion to another protein. The marker protein can be detected by its enzymatic activity; for example β galactosidase can convert the substrate X-gal to a colored product, and luciferase can convert luciferin to a light-emitting product. The marker protein can be detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies.

The PUFAs produced using the subject methods and compositions may be found in the host plant tissue and/or plant part as free fatty acids or in conjugated forms such as acylglycerols, phospholipids, sulfolipids or glycolipids, and may be extracted from the host cell through a variety of means well-known in the art. Such means may include extraction with organic solvents, sonication, supercritical fluid extraction using for example carbon dioxide, and physical means such as presses, or combinations thereof. Of particular interest is extraction with hexane or methanol and chloroform. Where desirable, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products are enzymatically or chemically cleaved to release the free fatty acid or a less complex conjugate of interest, and are then subjected to further manipulations to produce a desired end product. Desirably, conjugated forms of fatty acids are cleaved with potassium hydroxide.

Surprisingly, as demonstrated more fully in the examples below, expression of the Mortierella Δ6 desaturase leads to the production of steariodonic acid in the oil extracted from seed tissue of host plant cells. Furthermore, expression of the Δ6 desaturase with additional desaturases provided for the enhanced production of SDA in the seed oil.

Thus, the present invention provides methods for the production of steariodonic acid (C18:4) in host plant cells. The methods allow for the production of SDA in host plant cells ranging from about 0.3 wt % to at least about 30 wt %, preferably, from about 5 wt % to at least about 25 wt %, more preferably from about 7 wt % to at least about 25 wt %. The SDA is preferably produced in the seed oil of host plants containing one or more expression constructs as described herein.

Furthermore, the present invention provides a novel source of plant oils containing steariodonic acid. The oils are preferably obtained from the plant seed tissue. The seed oils contain amounts of SDA ranging from about 0.3 wt % to at least about 30 wt %, preferably, from about 5 wt % to at least about 25 wt %, more preferably from about 7 wt % to at least about 25 wt %.

PURIFICATION OF FATTY ACIDS

If further purification is necessary, standard methods can be employed. Such methods include extraction, treatment with urea, fractional crystallization, HPLC, fractional distillation, silica gel chromatography, high speed centrifugation or distillation, or combinations of these techniques. Protection of reactive groups, such as the acid or alkenyl groups, may be done at any step through known techniques, for example alkylation or iodination. Methods used include methylation of the fatty acids to produce methyl esters. Similarly, protecting groups may be removed at any step. Desirably, purification of fractions containing ARA, DHA and EPA is accomplished by treatment with urea and/or fractional distillation.

USES OF FATTY ACIDS

The uses of the fatty acids of subject invention are several. Probes based on the DNAs of the present invention may find use in methods for isolating related molecules or in methods to detect organisms expressing desaturases. When used as probes, the DNAs or oligonucleotides need to be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practical to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of probe to target via isothermal titration calorimetry, or by coating the probe or target on a surface and detecting the change in scattering of light from the surface produced by binding of target or probe, respectively, as may be done with the BIAcore system.

The invention will be better understood by reference to the following non-limiting examples.

EXAMPLES

Example 1

Expression of ω-3 Desaturase from *C. Elegans* in Transgenic Plants

The Δ15/ω-3 activity of *Brassica napus* can be increased by the expression of an ω-3 desaturase from *C. elegans*. The fat-1 cDNA clone (Genbank accession L41807; Spychalla, J. P., Kinney, A. J., and Browse, J. 1997 P.N.A.S. 94, 1142–1147, SEQ ID NO:1 and SEQ ID NO:2) was obtained from John Browse at Washington State University. The fat-1 cDNA was modified by PCR to introduce cloning sites using the following primers:

Fat-1forward (SEQ ID NO:3):
  5'-CUACUACUACUACTGCAGACAATGGTCGCT CATTCCTCAGA-3'

Fat-1reverse (SEQ ID NO:4):
  5'-CAUCAUCAUCAUGCGGCCGCTTACTTGGCC TTTGCCTT-3'

These primers allowed the amplification of the entire coding region and added PstI and NotI sites to the 5'- and 3'-ends, respectively. The PCR product was subcloned into pAMP1 (GIBCOBRL) using the CloneAmp system (GIBCOBRL) to create pCGN5562. The sequence was verified by sequencing of both strands to be sure no changes were introduced by PCR.

A once base pair difference was observed in the fat-1 coding region from pCGN5562 vs. the fat-1 Genbank sequence. The C at position 705 of the fat-1 sequence was changed to an A in pCGN5562. This creates a change of a GAC codon to GAA, changing the Asp residue at position 231 of fat-1 to a Glu residue. This identical change was observed in products of two independent PCR reactions using fat-1 template and most likely is not a result of PCR mis-incorporation of a nucleotide. For seed specific expression, the Fat-1 coding region was cut out of pCGN5562 as a PstI/NotI fragment and inserted between the PstI/NotI sites of the binary vector, pCGN8623, to create pCGN5563. PCGN5563 can be introduced into *Brassica napus* via Agrobacterium-mediated transformation.

Construction of pCGN8623

The polylinker region of the napin promoter cassette, pCGN7770, was replaced by ligating the following oligonucleotides:

5'-TCGACCTGCAGGAAGCTTGCGGCCGCGGATCC-3' (SEQ ID NO:5) and

5'-TCGAGGATCCGCGGCCGCAAGCTTCCTGCAGG-3' (SEQ ID NO:6).

These oligonucleotides were ligated into SalI/XhoI-digested pCGN7770 to produce pCGN8619. These oligos encode BamHI, NotI, HindIII, and PstI restriction sites. pCGN8619 contains the oligos oriented such that the PstI site is closest to the napin 5' regulatory region. A fragment containing the napin 5' regulatory region, polylinker, and napin 3' region was removed from pCGN8619 by digestion with Asp718I. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8623.

To produce high levels of stearidonic acid in Brassica, the *C. elegans* ω-3 desaturase can be combined with Δ6- and Δ12-desaturases from *Mortierella alpina*. PCGN5563-transformed plants may be crossed with pCGN5544-transformed plants expressing the Δ6-and Δ12-desaturases, described below.

The resulting F1 seeds can be analyzed for stearidonic acid content and selected F1 plants can be used for self-pollination to produce F2 seed, or as donors for production of dihaploids, or additional crosses.

An alternative method to combine the fat-1 cDNA with *M. alpina* Δ6 and Δ12 desaturases is to combine them on one T-DNA for transformation. The fat-1 coding region from pCGN5562 can be cut out as a PstI/NotI fragment and inserted into PstI/NotI digested pCGN8619. The transcriptional unit consisting of the napin 5' regulatory region, the fat-1 coding region, and the napin 3'-regulatory region can be cut out as a Sse8387I fragment and inserted into pCGN5544 cut with Sse8387I. The resulting plasmid would contain three napin transcriptional units containing the *C. elegans* ω-3 desaturase, *M. alpina* Δ6 desaturase, and *M. alpina* Δ12 desaturase, all oriented in the same direction as the 35S/nptII/tml transcriptional unit used for selection of transformed tissue.

Example 2

Over-Expression of Δ15-desaturase Activity in Transgenic Canola

The Δ15-desaturase activity of *Brassica napus* can be increased by over-expression of the Δ15-desaturase cDNA clone.

A *B. napus* Δ15-desaturase cDNA clone was obtained by PCR amplification of first-strand cDNA derived from *B. napus* cv. 212/86. The primers were based on published sequence: Genbank #L01418 Arondel et al, 1992 Science 258:1353–1355 (SEQ ID NO:7 and SEQ ID NO:8).

The following primers were used:

Bnd15-FORWARD (SEQ ID NO:9)
5'-CUACUACUACUAGAGCTCAGCGATGGTTGTTGCTATGGAC-3'

Bnd15-REVERSE (SEQ ID NO:10)
5'-CAUCAUCAUCAUGAATTCTTAATTGATTTTAGATTTG-3'

These primers allowed the amplification of the entire coding region and added SacI and EcoRI sites to the 5'- and 3'-ends, respectively The PCR product was subcloned into pAMP1 (GIBCOBRL) using the CloneAmp system (GIBCOBRL) to create pCGN5520. The sequence was verified by sequencing of both strands to be sure that the open reading frame remained intact. For seed specific expression, the Δ15-desaturase coding region was cut out of pCGN5520 as a BamHI/SalI fragment and inserted between the BglII and XhoI sites of the pCGN7770, to create pCGN5557. The PstI fragment of pCGN5557 containing the napin 5'-regulatory region, *B. napus* Δ15-desaturase, and napin 3'-regulatory region was inserted into the PstI site of the binary vector, pCGN5138 to produce pCGN5558. pCGN5558 was introduced into *Brassica napus* via Agrobacterium-mediated transformation.

To produce high levels of stearidonic acid in Brassica, the Δ15-desaturase can be combined with Δ6- and Δ12-desaturases from *Mortierella alpina*. PCGN5558-transformed plants may be crossed with pCGN5544-transformed plants expressing the Δ6 and Δ12-desaturases. The resulting F1 seeds are analyzed for stearidonic acid content. GC-FAME analysis of F1 half-seeds revealed a significant accumulation of SDA in the seed oil of the Brassica lines. SDA levels (18:4) of greater than approximately 25% were obtained in hemizygous lines and are provided in Table 1. Selected F1 plants can be used for self-pollination to produce F2 seed, or as donors for production of dihaploids, or additional crosses.

TABLE 1

| Strain ID* | 16:0 | 18:0 | 18:1 | 18:2 | 18:2 C912 | 18:3 | 18:3 C91215 | 18:3 C6912 | 18:4 | 20:0 | 20:1 | 20:2 | 22:0 | 22:1 | 22:2 |
|---|---|---|---|---|---|---|---|---|---|---|---|---|---|---|---|
| (5558-SP30021-26 X 5544-LP30108-6-16-1-3) | 6 | 1.34 | 2.97 | 9.58 | 9.58 | 52.79 | 34.76 | 18.03 | 25.21 | 0.7 | 0.56 | 0.16 | 0.41 | 0.03 | 0 |
| (5558-SP30021-26 X 5544-LP30108-6-16-1-3) | 4.45 | 0.86 | 10.42 | 9.06 | 9.06 | 49.08 | 25.68 | 23.4 | 23.45 | 0.5 | 0.84 | 0.55 | 0.49 | 0 | 0.03 |
| (5558-SP30021-26 X 5544-LP30108-6-16-1-3) | 5.8 | 2.36 | 12.5 | 11.13 | 11.13 | 47.47 | 18.86 | 28.61 | 17.55 | 1.01 | 0.86 | 0.3 | 0.85 | 0 | 0.07 |
| (5558-SP30021-26 X 5544-LP30108-6-16-1-3) | 3.65 | 0.66 | 14.26 | 14.97 | 14.97 | 50.94 | 23.3 | 27.64 | 13.22 | 0.43 | 0.88 | 0.23 | 0.48 | 0.04 | 0 |
| (5558-SP30021-26 X 5544-LP30108-6-16-1-3) | 4.86 | 2.42 | 18.74 | 14.23 | 14.23 | 46.22 | 23 | 23.22 | 10.67 | 0.89 | 0.92 | 0.18 | 0.7 | 0.02 | 0 |

TABLE 1-continued

| Strain ID* | 16:0 | 18:0 | 18:1 | 18:2 | 18:2 | 18:3 | 18:3 | 18:3 | 18:4 | 20:0 | 20:1 | 20:2 | 22:0 | 22:1 | 22:2 |
|---|---|---|---|---|---|---|---|---|---|---|---|---|---|---|---|
| | | | | | | | C912 | C91215-ALA | C6912-GLA | | | | | | |
| (5558-SP30021-26 X 5544-LP30108-6-16-1-3) | 6.57 | 1.07 | 16.79 | 14 | 14 | 48.98 | 32.88 | 16.09 | 10.24 | 0.52 | 0.94 | 0.22 | 0.39 | 0.02 | 0.01 |
| (5558-SP30021-26 X 5544-LP30108-6-16-1-3) | 5.85 | 2.09 | 8.81 | 19.12 | 19.12 | 50.89 | 12.03 | 38.86 | 9.09 | 1.39 | 0.78 | 0.45 | 1.23 | 0 | 0.04 |
| (5558-SP30021-26 X 5544-LP30108-6-16-1-3) | 4.69 | 2.04 | 17.46 | 21.1 | 21.1 | 43.38 | 24.28 | 19.1 | 8.5 | 0.73 | 0.96 | 0.37 | 0.56 | 0 | 0 |
| (5558-SP30021-26 X 5544-LP30108-6-16-1-3) | 5.43 | 1.69 | 16.59 | 22.2 | 22.2 | 44.4 | 16.57 | 27.83 | 6.34 | 0.9 | 1.03 | 0.32 | 0.81 | 0.03 | 0.05 |
| (5558-SP30021-26 X 5544-LP30108-6-16-1-3) | 4.28 | 1.34 | 18.83 | 27.24 | 27.24 | 40.54 | 20.91 | 19.63 | 5.03 | 0.73 | 0.88 | 0.27 | 0.7 | 0 | 0 |
| (5558-SP30021-26 X 5544-LP30108-6-16-1-3) | 4.47 | 1.38 | 21.43 | 26.89 | 26.89 | 39.04 | 18.78 | 20.26 | 4.06 | 0.73 | 0.91 | 0.41 | 0.48 | 0 | 0 |
| (5558-SP30021-26 X 5544-LP30108-6-16-1-3) | 4.77 | 1.12 | 18.4 | 31.1 | 31.1 | 38.51 | 19.62 | 18.88 | 3.52 | 0.64 | 0.8 | 0.21 | 0.7 | 0 | 0 |
| (5558-SP30021-26 X 5544-LP30108-6-16-1-3) | 4.34 | 1.86 | 24.73 | 35.49 | 35.49 | 28.79 | 10.79 | 18 | 1.91 | 0.67 | 1.07 | 0.45 | 0.48 | 0 | 0.02 |
| (5558-SP30021-26 X 5544-LP30108-6-16-1-3) | 4.71 | 1.75 | 20.72 | 34.68 | 34.68 | 34.01 | 4.65 | 29.36 | 1.62 | 0.71 | 0.89 | 0.1 | 0.63 | 0 | 0 |
| (5558-SP30021-26 X 5544-LP30108-6-16-1-3) | 4.3 | 0.8 | 40.79 | 14.34 | 14.34 | 37 | 36.88 | 0.12 | 0 | 0.43 | 1.47 | 0.29 | 0.29 | 0 | 0 |
| (5558-SP30021-19 X 5544-LP30108-6-16-1-1) | 6.61 | 1.5 | 22.09 | 11.23 | 11.23 | 39.9 | 25.84 | 14.06 | 16.25 | 0.75 | 0.75 | 0.27 | 0.57 | 0 | 0 |
| (5558-SP30021-19 X 5544-LP30108-6-16-1-1) | 4.64 | 1.89 | 22.73 | 15.12 | 15.12 | 44.48 | 32.21 | 12.27 | 8.78 | 0.73 | 0.89 | 0.23 | 0.43 | 0 | 0 |
| (5558-SP30021-19 X 5544-LP30108-6-16-1-1) | 5.51 | 1.45 | 24.82 | 17.79 | 17.79 | 41.84 | 27.46 | 14.38 | 6.45 | 0.59 | 0.82 | 0.23 | 0.39 | 0 | 0 |
| (5558-SP30021-19 X 5544-LP30108-6-16-1-1) | 4.06 | 1.67 | 26.39 | 16.93 | 16.93 | 42.64 | 32.65 | 9.99 | 6 | 0.64 | 0.96 | 0.24 | 0.41 | 0 | 0 |
| (5558-SP30021-19 X 5544-LP30108-6-16-1-1) | 5.24 | 1.44 | 22.2 | 20.02 | 20.02 | 42.76 | 28.69 | 14.07 | 5.98 | 0.67 | 0.79 | 0.26 | 0.45 | 0 | 0 |
| (5558-SP30021-19 X 5544-LP30108-6-16-1-1) | 5.34 | 2.2 | 22.68 | 18.6 | 18.6 | 43.14 | 31.45 | 11.69 | 5.5 | 0.82 | 0.87 | 0.25 | 0.53 | 0 | 0 |
| (5558-SP30021-19 X 5544-LP30108-6-16-1-1) | 3.98 | 2.9 | 25.23 | 21.21 | 21.21 | 38.78 | 24.6 | 14.18 | 4.98 | 1.02 | 1.04 | 0.24 | 0.57 | 0 | 0 |
| (5558-SP30021-19 X 5544-LP30108-6-16-1-1) | 3.94 | 1.77 | 28.92 | 20.89 | 20.89 | 37.02 | 21.71 | 15.32 | 4.96 | 0.64 | 1.09 | 0.3 | 0.43 | 0 | 0 |
| (5558-SP30021-19 X 5544-LP30108-6-16-1-1) | 5.12 | 1.24 | 27.7 | 19.02 | 19.02 | 40.2 | 31.05 | 9.16 | 4.76 | 0.48 | 0.77 | 0.23 | 0.35 | 0 | 0 |
| (5558-SP30021-19 X 5544-LP30108-6-16-1-1) | 4.16 | 1.52 | 28.59 | 21.99 | 21.99 | 36.85 | 23.33 | 13.53 | 4.55 | 0.6 | 0.98 | 0.27 | 0.41 | 0 | 0 |
| (5558-SP30021-19 X 5544-LP30108-6-16-1-1) | 4.91 | 1.32 | 30.46 | 18.01 | 18.01 | 38.59 | 30.23 | 8.36 | 4.34 | 0.58 | 0.93 | 0.25 | 0.4 | 0 | 0 |
| (5558-SP30021-36 X 5544-LP30108-6-16-1-1) | 3.66 | 1.52 | 29.52 | 20.52 | 20.52 | 36.61 | 20.09 | 16.52 | 5.63 | 0.67 | 1.12 | 0.14 | 0.52 | 0 | 0 |
| (5558-SP30021-36 X 5544-LP30108-6-16-1-1) | 5.09 | 1.81 | 25.81 | 21.54 | 21.54 | 38.2 | 22.52 | 15.68 | 4.92 | 0.75 | 0.96 | 0.12 | 0.57 | 0.02 | 0 |
| (5558-SP30021-36 X 5544-LP30108-6-16-1-1) | 3.77 | 1.5 | 29.79 | 22.36 | 22.36 | 35.46 | 14.84 | 20.62 | 4.39 | 0.74 | 1.17 | 0.18 | 0.59 | 0.02 | 0 |
| (5558-SP30021-36 X 5544-LP30108-6-16-1-1) | 3.71 | 1.45 | 32.18 | 23.86 | 23.86 | 32.32 | 17 | 15.32 | 3.92 | 0.63 | 1.12 | 0.15 | 0.5 | 0.02 | 0 |
| (5558-SP30021-36 X 5544-LP30108-6-16-1-1) | 3.55 | 1.56 | 33.27 | 25.21 | 25.21 | 30.69 | 16.63 | 14.06 | 3.08 | 0.68 | 1.2 | 0.16 | 0.54 | 0.03 | 0 |
| (5558-SP30021-36 X 5544-LP30108-6-16-1-1) | 4.04 | 1.52 | 33.63 | 24.47 | 24.47 | 30.72 | 18.19 | 12.53 | 3.07 | 0.63 | 1.17 | 0.14 | 0.46 | 0 | 0 |
| (5558-SP30021-36 X 5544-LP30108-6-16-1-1) | 3.67 | 1.58 | 31.98 | 26.13 | 26.13 | 30.89 | 15.92 | 14.97 | 3.05 | 0.69 | 1.21 | 0.16 | 0.51 | 0 | 0 |
| (5558-SP30021-36 X 5544-LP30108-6-16-1-1) | 3.58 | 1.8 | 30.2 | 27.22 | 27.22 | 31.42 | 15.48 | 15.94 | 2.85 | 0.79 | 1.21 | 0.17 | 0.61 | 0.02 | 0.01 |
| (5558-SP30021-36 X 5544-LP30108-6-16-1-1) | 4.68 | 1.41 | 28.32 | 28 | 28 | 32.22 | 14.92 | 17.3 | 2.74 | 0.65 | 1.1 | 0.18 | 0.53 | 0.01 | 0 |
| (5558-SP30021-36 X 5544-LP30108-6-16-1-1) | 3.5 | 1.46 | 34.13 | 25.92 | 25.92 | 29.7 | 16.77 | 12.93 | 2.65 | 0.67 | 1.26 | 0.15 | 0.51 | 0.01 | 0 |
| (5558-SP30021-36 X 5544-LP30108-6-16-1-1) | 3.9 | 1.68 | 33.44 | 26.18 | 26.18 | 29.43 | 16.11 | 13.31 | 2.6 | 0.72 | 1.23 | 0.18 | 0.5 | 0.02 | 0 |
| (5558-SP30021-36 X 5544-LP30108-6-16-1-1) | 3.82 | 1.71 | 31.84 | 27.78 | 27.78 | 29.49 | 15.28 | 14.2 | 2.59 | 0.73 | 1.19 | 0.16 | 0.55 | 0.02 | 0 |
| (5558-SP30021-36 X 5544-LP30108-6-16-1-1) | 3.6 | 1.78 | 29.45 | 28.14 | 28.14 | 31.64 | 12.83 | 18.81 | 2.57 | 0.76 | 1.21 | 0.17 | 0.58 | 0 | 0 |

An alternative method to combine the *B. napus* Δ15-desaturase with *M. alpina* Δ6 and Δ12 desaturases is to combine them on one T-DNA for transformation. The transcription cassette consisting of the napin 5'-regulatory region, the Δ15-desaturase coding region, and the napin 3'-regulatory region can be cut out of pCGN5557 as a SwaI fragment and inserted into SwaI-digested pCGN5544. The resulting plasmid, pCGN5561, contains three napin transcriptional units containing the M. alpina Δ6 desaturase, the B. napus Δ15-desaturase, and the M. alpina Δ12 desaturase, all oriented in the same direction as the 35S/nptII/tml transcriptional unit used for selection of transformed tissue. In addition, the C. elegans ω-3 desaturase coding sequence was also cloned into pCGN5544 to create the construct pCGN5565.

Pooled T2 seeds of plants containing 5561 contain significant amounts of SDA (18:4), shown in Table 2. Levels of greater than about 7% SDA are obtained in pooled 5561 segregating seed. Furthermore, significant levels of SDA were obtained from seeds of 5565 Brassica lines, also shown in Table 2. As shown in Table 2, with constructs 5561 and 5565, levels of SDA ranging from about 0.8 wt % to greater than about 7 wt % can be obtained.

The Ma29 desaturase cDNA was modified by PCR to introduce convenient restriction sites for cloning. The desaturase coding region has been inserted into a d35 cassette under the control of the double 35S promoter for expression in Brassica leaves (pCGN5525) following standard protocols (see U.S. Pat. No. 5,424,200 and U.S. Pat. No. 5,106,739). Transgenic Brassica plants containing pCGN5525 were generated following standard protocols (see U.S. Pat. No. 5,188,958 and U.S. Pat. No. 5,463,174).

In the first experiment, three plants were used: a control, LPO04-1, and two transgenics, 5525-23 and 5525-29. LP004 is a low-linolenic Brassica variety. Leaves of each were selected for one of three treatments: water, GLA or DGLA. GLA and DGLA were purchased as sodium salts from NuChek Prep and dissolved in water at 1 mg/ml. Aliquots were capped under N2 and stored at −70 degrees C. Leaves were treated by applying a 50 µl drop to the upper

TABLE 2

| STRAIN ID | 16:0 | 16:1 | 18:0 | 18:1 | 18:2 C6,9 | 18:2 C9,12 | 18:3 C6,9,12 | 18:3 C9,12,15 | 18:4 | 20:0 | 20:1 | 20:2 | 22:0 | 22:1 | 22:2 |
|---|---|---|---|---|---|---|---|---|---|---|---|---|---|---|---|
| 5561-6 | 4.46 | 0.21 | 3.5 | 22.85 | 0 | 18.33 | 18.71 | 21.61 | 7.79 | 1.04 | 0.76 | 0.19 | 0.47 | 0 | 0 |
| 5561-4 | 4.14 | 0.15 | 2.62 | 33.07 | 0 | 21.07 | 17.61 | 14.56 | 4.39 | 0.87 | 0.92 | 0.14 | 0.39 | 0 | 0.02 |
| 5561-2 | 4.26 | 0.15 | 2.21 | 30.42 | 0 | 22.02 | 21.06 | 12.88 | 4.25 | 0.89 | 0.98 | 0.2 | 0.51 | 0 | 0.02 |
| 5561-8 | 4.29 | 0.18 | 2 | 33.05 | 0 | 22.44 | 16.23 | 15.3 | 3.95 | 0.84 | 0.96 | 0.19 | 0.43 | 0 | 0.04 |
| 5561-3 | 3.95 | 0.12 | 2.04 | 32.93 | 0 | 24.48 | 17.42 | 13.33 | 3.27 | 0.79 | 0.94 | 0.21 | 0.4 | 0.03 | 0.03 |
| 5561-7 | 4.26 | 0.17 | 2.02 | 38.4 | 0 | 23.3 | 13.35 | 13.3 | 2.73 | 0.75 | 1.06 | 0.16 | 0.41 | 0 | 0 |
| 5561-13 | 4.38 | 0.18 | 1.86 | 58.94 | 0.65 | 13.98 | 7.1 | 8.26 | 1.88 | 0.77 | 1.27 | 0.29 | 0.35 | 0.03 | 0 |
| 5561-15 | 4.29 | 0.15 | 2.3 | 40.96 | 0 | 26.63 | 8.58 | 12.98 | 1.51 | 0.83 | 1.07 | 0.19 | 0.45 | 0 | 0.02 |
| 5561-1 | 4.25 | 0.15 | 1.91 | 47.41 | 0 | 24.46 | 5.56 | 12.81 | 1 | 0.72 | 1.14 | 0.15 | 0.39 | 0 | 0 |
| 5561-5 | 4.07 | 0.16 | 1.96 | 52.29 | 0 | 20.88 | 5.02 | 12.17 | 0.97 | 0.72 | 1.16 | 0.21 | 0.28 | 0 | 0.06 |
| CONTROL | 3.89 | 0.21 | 1.65 | 58.48 | 0 | 22.44 | 0 | 11.03 | 0 | 0.6 | 1.15 | 0.16 | 0.27 | 0.01 | 0 |

| STRAIN ID | 16:0 | 18:0 | 18:1 | 18:2-C69 | 18:2-LA | 18:3-GLA | 18:3-ALA | 18:4 | 20:0 |
|---|---|---|---|---|---|---|---|---|---|
| 5565-SP30021-7 | 4.03 | 1.93 | 41.24 | 0.43 | 14.46 | 21.39 | 6.62 | 7.38 | 0.68 |
| 5565-SP30021-12 | 3.95 | 2.46 | 40.19 | 0 | 30.35 | 7.3 | 10.92 | 2.57 | 0.7 |
| 5565-SP30021-9 | 4.03 | 1.82 | 35.76 | 0 | 33.49 | 8.63 | 11.58 | 2.54 | 0.51 |
| 5565-SP30021-3 | 3.86 | 1.8 | 32.3 | 0 | 35.57 | 11.3 | 10.05 | 2.37 | 0.61 |
| 5565-SP30021-1 | 3.98 | 1.92 | 59.99 | 1.84 | 11.24 | 8.07 | 7.46 | 2.32 | 0.76 |
| 5565-SP30021-8 | 4.67 | 1.72 | 38.95 | 0 | 30.38 | 8.99 | 10.83 | 2.25 | 0.52 |
| 5565-SP30021-10 | 4.03 | 1.43 | 47.04 | 0 | 26.96 | 5.97 | 11.1 | 1.35 | 0.52 |
| 5565-SP30021-6 | 3.87 | 1.77 | 46.73 | 0 | 28.79 | 5.31 | 10.4 | 0.79 | 0.56 |
| CONTROL | 3.89 | 1.65 | 58.48 | 0 | 22.44 | 0 | 11.03 | 0 | 0.6 |

Example 3

Expression of Δ5 Desaturase in Plants Expression in Leaves

Ma29 is a putative M. alpina Δ5 desaturase as determined by sequence homology (SEQ ID NO:11 and SEQ ID NO:12). This experiment was designed to determine whether leaves expressing Ma29 (as determined by Northern) were able to convert exogenously applied DGLA (20:3) to ARA (20:4).

surface and gently spreading with a gloved finger to cover the entire surface. Applications were made approximately 30 minutes before the end of the light cycle to minimize any photo-oxidation of the applied fatty acids. After 6 days of treatment one leaf from each treatment was harvested and cut in half through the mid rib. One half was washed with water to attempt to remove unincorporated fatty acid. Leaf samples were lyophilized overnight, and fatty acid composition determined by gas chromatography (GC). The results are shown in Table 3.

TABLE 3

Fatty Acid Analysis of Leaves from Ma29 Transgenic Brassica Plants

| Treatment | SPL # | 16:00 % | 16:01 % | 18:00 % | 18:01 % | 18:02 % | 18:3g % | 18:03 % | 18:04 % | 20:00 % | 20:01 % |
|---|---|---|---|---|---|---|---|---|---|---|---|
| Water | 33 | 12.95 | 0.08 | 2.63 | 2.51 | 16.76 | 0 | 45.52 | 0 | 0.09 | 0 |
| | 34 | 13.00 | 0.09 | 2.67 | 2.56 | 16.86 | 0 | 44.59 | 0 | 0.15 | 0 |
| | 35 | 14.13 | 0.09 | 2.37 | 2.15 | 16.71 | 0 | 49.91 | 0 | 0.05 | 0.01 |
| | 36 | 13.92 | 0.08 | 2.32 | 2.07 | 16.16 | 0 | 50.25 | 0 | 0.05 | 0 |
| | 37 | 13.79 | 0.11 | 2.10 | 2.12 | 15.90 | 0.08 | 46.29 | 0 | 0.54 | 0.01 |
| | 38 | 12.80 | 0.09 | 1.94 | 2.08 | 14.54 | 0.11 | 45.61 | 0 | 0.49 | 0.01 |

TABLE 3-continued

Fatty Acid Analysis of Leaves from Ma29 Transgenic Brassica Plants

| | | | | | | | | | | | |
|---|---|---|---|---|---|---|---|---|---|---|---|
| GLA | 39 | 12.10 | 0.09 | 2.37 | 2.10 | 14.85 | 1.63 | 43.66 | 0 | 0.53 | 0 |
| | 40 | 12.78 | 0.10 | 2.34 | 2.22 | 15.29 | 1.72 | 47.22 | 0 | 0.50 | 0.02 |
| | 41 | 13.71 | 0.07 | 2.68 | 2.16 | 15.92 | 2.12 | 46.55 | 0 | 0.09 | 0 |
| | 42 | 14.10 | 0.07 | 2.75 | 2.35 | 16.66 | 1.56 | 46.41 | 0 | 0.09 | 0.01 |
| | 43 | 13.62 | 0.09 | 2.22 | 1.94 | 14.68 | 2.42 | 46.69 | 0 | 0.51 | 0.01 |
| | 44 | 14.92 | 0.09 | 2.20 | 2.17 | 15.22 | 2.30 | 46.05 | 0 | 0.53 | 0.02 |
| DGLA | 45 | 12.45 | 0.14 | 2.30 | 2.28 | 15.65 | 0.07 | 44.62 | 0 | 0.12 | 0.01 |
| | 46 | 12.67 | 0.15 | 2.69 | 2.50 | 15.96 | 0.09 | 42.77 | 0 | 0.56 | 0.01 |
| | 47 | 12.56 | 0.23 | 3.40 | 1.98 | 13.57 | 0.03 | 45.52 | 0 | 0.51 | 0.01 |
| | 48 | 13.07 | 0.24 | 3.60 | 2.51 | 13.54 | 0.04 | 45.13 | 0 | 0.50 | 0.01 |
| | 49 | 13.26 | 0.07 | 2.81 | 2.34 | 16.04 | 0.04 | 43.89 | 0 | 0.59 | 0 |
| | 50 | 13.53 | 0.07 | 2.84 | 2.41 | 16.07 | 0.02 | 44.90 | 0 | 0.60 | 0.01 |

| Treatment | SPL # | 20:02 % | 20:03 % | 20:04 % | 20:05 % | 22:00 % | 22:01 % | 22:02 % | 22:03 % | 22:06 % | 24:0 % | 24:1 % |
|---|---|---|---|---|---|---|---|---|---|---|---|---|
| Water | 33 | 0 | 0 | 0.29 | 0 | 0.01 | 0.09 | 16.26 | 0 | 0 | 0.38 | 0.18 |
| | 34 | 0.01 | 0 | 0.2 | 0 | 0.14 | 0.10 | 16.82 | 0.02 | 0.05 | 0.36 | 0.27 |
| | 35 | 0.01 | 0 | 0.25 | 0 | 0.12 | 0.06 | 11.29 | 0.04 | 0.05 | 0.29 | 0.25 |
| | 36 | 0 | 0.01 | 0.26 | 0 | 0.07 | 0.04 | 11.82 | 0.03 | 0.36 | 0.28 | 0.21 |
| | 37 | 0.02 | 0 | 0.21 | 0 | 0.18 | 0.08 | 15.87 | 0.06 | 0.20 | 0.30 | 0.17 |
| | 38 | 0.01 | 0 | 0.24 | 0 | 0.15 | 0.07 | 13.64 | 0.09 | 0.08 | 5.89 | 0.23 |
| GLA | 39 | 0.02 | 0.01 | 0.27 | 0 | 0.10 | 0.08 | 16.25 | 3.42 | 0.19 | 0.37 | 0.17 |
| | 40 | 0.01 | 0 | 0.27 | 0 | 0.10 | 0.10 | 14.74 | 0.05 | 0.10 | 0.36 | 0.14 |
| | 41 | 0 | 0 | 0.27 | 0 | 0.20 | 0.10 | 13.15 | 0.13 | 0.29 | 0.33 | 0.20 |
| | 42 | 0 | 0 | 0.28 | 0 | 0.11 | 0.11 | 12.60 | 0.02 | 0.24 | 0.38 | 0.13 |
| | 43 | 0.01 | 0 | 0.28 | 0 | 0.10 | 0.03 | 14.73 | 0.01 | 0.24 | 0.34 | 0.14 |
| | 44 | 0.02 | 0 | 0.26 | 0 | 0.13 | 0.07 | 14.43 | 0.05 | 0.16 | 0.33 | 0.17 |
| DGLA | 45 | 0.06 | 1.21 | 0.26 | 0 | 0.07 | 0.07 | 18.67 | 0.02 | 0.21 | 0.36 | 0.13 |
| | 46 | 0 | 1.94 | 0.27 | 0 | 0.11 | 0.09 | 17.97 | 0.09 | 0.39 | 0.41 | 0.11 |
| | 47 | 0.01 | 0.69 | 0.96 | 0 | 0.11 | 0.07 | 17.96 | 0 | 0.22 | 0.49 | 0.20 |
| | 48 | 0.01 | 0.70 | 0.74 | 0 | 0.14 | 0.09 | 17.14 | 0.05 | 0.32 | 0.52 | 0.10 |
| | 49 | 0 | 0.35 | 1.11 | 0 | 0.10 | 0.07 | 17.26 | 0.07 | 0.23 | 0.39 | 0.18 |
| | 50 | 0 | 0.20 | 0.87 | 0 | 0.21 | 0.07 | 15.73 | 0.04 | 0.15 | 0.37 | 0.18 |

Leaves treated with GLA contained from 1.56 to 2.4 wt % GLA. The fatty acid analysis showed that the lipid composition of control and transgenic leaves was essentially the same. Leaves of control plants treated with DGLA contained 1.2–1.9 w % DGLA and background amounts of ARA (0.26–0.27 wt %). Transgenic leaves contained only 0.2–0.7 wt % DGLA, but levels of ARA were increased (0.74–1.1 wt %) indicating that the DGLA was converted to ARA in these leaves.

Expression in Seed

The purpose of this experiment was to determine whether a construct with the seed specific napin promoter would enable expression in seed.

The Ma29 cDNA was modified by PCR to introduce XhoI cloning sites upstream and downstream of the start and stop codons, respectively, using the following primers:

Madxho-forward (SEQ ID NO:13):
  5'-CUACUACUACUACTCGAGCAAGATGGGAA CGGACCAAGG

Madxho-reverse (SEQ ID NO:14):
  5'-CAUCAUCAUCAUCTCGAGCTACTCTTCCTT GGGACGGAG

The PCR product was subcloned into pAMP1 (GIBCOBRL) using the CloneAmp system (GIBCOBRL) to create pCGN5522 and the Δ5 desaturase sequence was verified by sequencing of both strands.

For seed-specific expression, the Ma29 coding region was cut out of pCGN5522 as an XhoI fragment and inserted into the SalI site of the napin expression cassette, pCGN3223, to create pCGN5528. The HindIII fragment of pCGN5528 containing the napin 5' regulatory region, the Ma29 coding region, and the napin 3' regulatory region was inserted into the HindIII site of pCGN1557 to create pCGN5531. Two copies of the napin transcriptional unit were inserted in tandem. This tandem construct can permit higher expression of the desaturases per genetic loci. pCGN5531 was introduced into *Brassica napus* cv.LP004 via Agrobacterium mediated transformation.

The fatty acid composition of twenty-seed pools of mature T2 seeds was analyzed by GC. Table 2 shows the results obtained with independent transformed lines as compared to non-transformed LP004 seed. The transgenic seeds containing pCGN5531 contain two fatty acids that are not present in the control seeds, identified as taxoleic acid (5,9-18:2) and pinolenic acid (5,9,12-18:3), based on their elution relative to oleic and linoleic acid. These would be the expected products of Δ5 desaturation of oleic and linoleic acids. No other differences in fatty acid composition were observed in the transgenic seeds.

Example 4

Production of D5-desaturated Fatty Acids in Transgenic Plants

The construction of pCGN5531 (Δ5-desaturase) and fatty acid composition of T2 seed pools is described in Example 3. This example takes the seeds through one more generation and discusses ways to maximize the Δ5-desaturated fatty acids.

Example 3 describes the fatty acid composition of T2 seed pools of pCGN5531-transformed *B. napus* cv. LP004 plants. To investigate the segregation of Δ5-desaturated fatty acids in the T2 seeds and to identify individual plants to be taken on to subsequent generations, half-seed analysis was done. Seeds were germinated overnight in the dark at 30 degrees on water-soaked filter paper. The outer cotyledon was excised for GC analysis and the rest of the seedling was planted in soil. Results of some of these analyses are shown in the accompanying Table 4. Δ5,9-18:2 accumulated to as high as 12% of the total fatty acids and A 5,9,12–18:3 accumulated to up to 0.77% of the fatty acids. These and other individually selected T2 plants were grown in the greenhouse to produce T3 seed.

ella alpina was obtained by random sequencing of clones from the M. alpina cDNA library. The Ma524 cDNA was modified by PCR to introduce cloning sites using the following primers:

Ma524PCR-1 (SEQ ID NO:15)
5'-CUACUACUACUAUCTAGACTCGAGACCATG GCTGCTGCT CCAGTGTG

Ma524PCR-2 (SEQ ID NO:16)
5'-CAUCAUCAUCAUAGGCCTCGAGTTACTGCG CCTTACCCAT

TABLE 4

| | Composition of T2 Pooled Seed | | | | | | | | | | | | | |
|---|---|---|---|---|---|---|---|---|---|---|---|---|---|---|
| | 16:0 % | 16:1 % | 18:0 % | 18:1 % Δ | Δ5,9 18:2 % | 18:2 % Δ | Δ5,9,12 18:3 % | 18:3 % | 20:0 % | 20:1 % | 20:2 % | 22:0 % | 22:1 % | 24:0 % |
| LP004 control | 3.86 | 0.15 | 3.05 | 69.1 | 0 | 18.51 | 0.01 | 1.65 | 1.09 | 1.40 | 0.03 | 0.63 | 0.05 | 0.42 |
| 5531-1 | 4.26 | 0.15 | 3.23 | 62.33 | 4.07 | 21.44 | 0.33 | 1.38 | 0.91 | 1.04 | 0.05 | 0.41 | 0.03 | 0.27 |
| 5531-2 | 3.78 | 0.14 | 3.37 | 66.18 | 4.57 | 17.31 | 0.27 | 1.30 | 1.03 | 1.18 | 0 | 0.47 | 0.01 | 0.30 |
| 5531-6 | 3.78 | 0.13 | 3.47 | 63.61 | 6.21 | 17.97 | 0.38 | 1.34 | 1.04 | 1.14 | 0.05 | 0.49 | 0.02 | 0.26 |
| 5531-10 | 3.96 | 0.17 | 3.28 | 63.82 | 5.41 | 18.58 | 0.32 | 1.43 | 0.98 | 1.11 | 0.02 | 0.50 | 0 | 0.31 |
| 5531-16 | 3.91 | 0.17 | 3.33 | 64.31 | 5.03 | 18.98 | 0.33 | 1.39 | 0.96 | 1.11 | 0 | 0.44 | 0 | 0 |
| 5531-28 | 3.81 | 0.13 | 2.58 | 62.64 | 5.36 | 20.95 | 0.45 | 1.39 | 0.83 | 1.15 | 0.01 | 0.36 | 0.05 | 0.21 |

| Fatty acid analysis of selected T2 half-seeds from pCGN5531-LP004 events | | | | | | | | | | | |
|---|---|---|---|---|---|---|---|---|---|---|---|
| CYCLE ID | SPL NO | STRAIN ID | 12:0 | 14:0 | 16:0 | 16:1 | 18:0 | 18:1 | 18:2 Δ5,9 | 18:2 Δ9,12 | 18:3 Δ5,9,12 | 18:3 Δ9,12,15 |
| 97XX1539 | 93 | 5531-LP004-6 | 0.03 | 0.07 | 3.92 | 0.17 | 3.5 | 61.32 | 12.22 | 15.36 | 0.77 | 1.36 |
| 97XX1539 | 29 | 5531-LP004-6 | 0.01 | 0.04 | 3.6 | 0.09 | 3.23 | 63.77 | 10.63 | 14.47 | 0 | 1.22 |
| 97XX1539 | 38 | 5531-LP004-6 | 0.01 | 0.05 | 3.71 | 0.09 | 3.02 | 65.13 | 10.57 | 13.98 | 0 | 1.06 |
| 97XX1539 | 41 | 5531-LP004-6 | 0.01 | 0.05 | 3.64 | 0.07 | 3.22 | 62.51 | 9.7 | 16.63 | 0 | 1.28 |
| 97XX1539 | 18 | 5531-LP004-6 | 0.02 | 0.06 | 3.69 | 0.09 | 3.36 | 63.79 | 9.63 | 15.29 | 0.63 | 1.15 |
| 97XX1539 | 85 | 5531-LP004-6 | 0.01 | 0.06 | 3.6 | 0.09 | 3.54 | 64.81 | 9.54 | 13.69 | 0.6 | 1.26 |
| 98GC0023 | 98 | 5531-LP004-23 | 0.01 | 0.05 | 3.5 | 0.09 | 3.12 | 64.97 | 9.92 | 13.62 | 0.55 | 1.25 |
| 98GC0023 | 32 | 5531-LP004-23 | 0.01 | 0.05 | 3.43 | 0.08 | 2.62 | 65.21 | 9.83 | 14.28 | 0.59 | 1.15 |
| 98GC0023 | 78 | 5531-LP004-23 | 0.01 | 0.05 | 3.45 | 0.07 | 2.78 | 64.97 | 9.34 | 14.69 | 0.58 | 1.17 |
| 98GC0023 | 86 | 5531-LP004-23 | 0.01 | 0.05 | 3.32 | 0.08 | 2.7 | 64.18 | 9.08 | 15.99 | 0.68 | 1.18 |
| 98GC0023 | 67 | 5531-LP004-23 | 0.01 | 0.04 | 3.49 | 0.08 | 3.03 | 64.14 | 8.78 | 15.95 | 0.62 | 1.08 |
| 98GC0023 | 52 | 5531-LP004-23 | 0.01 | 0.03 | 3.38 | 0.07 | 2.56 | 67.44 | 8.65 | 13.55 | 0.5 | 1.02 |

To maximize the accumulation of Δ5,9 18:2 in seed oil, the pCGN5531 construct could be introduced into a high oleic acid variety of canola. A high-oleic variety could be obtained by mutation, so-suppression, or antisense suppression of the Δ12 and Δ15 desaturases or other necessary co-factors.

To maximize accumulation of Δ5,9,12 18:3 in canola, the pCGN5531 construct could be introduced into a high linoleic strain of canola. This could be achieved by crossing pCGN5531-transformed plants with pCGN5542-(M. alpina Δ12-desaturase) transformed plants. Alternatively, the Δ5 and Δ12 desaturases could be combined on one T-DNA for transformation. The transcriptional unit consisting of the napin 5'-regulatory region, the M. alpina Δ12-desaturase coding region, and the napin 3'-regulatory region can be cut out of pCGN5541 as a NotI fragment. NotI/XbaI linkers could be ligated and the resulting fragment inserted into the XbaI site of pCGN5531. The resulting plasmid would contain three napin transcriptional units containing the M. alpina Δ12 desaturase, and two copies of the napin/M. alpina Δ5 desaturase/napin unit, all oriented in the same direction as the 35S/nptII/tml transcriptional unit used for selection of transformed tissue.

Example 5

Expression of M. Alpina Δ6 Desaturase in Brassica Napus

A nucleic acid sequence from a partial cDNA clone, Ma524, encoding a Δ6 fatty acid desaturase from Mortier- These primers allowed the amplification of the entire coding region and added XbaI and XhoI sites to the 5'-end and XhoI and StuI sites to the 3' end. The PCR product was subcloned into pAMP1 (GIBCOBRL) using the CloneAmp system (GIBCOBRL) to create pCGN5535 and the Δ6 desaturase sequence was verified by sequencing of both strands.

Construction of pCGN5544

Plant expression constructs were prepared to express the Mortierella alpina Δ6 desaturase and the Mortierella alpina Δ12 desaturase in a plant host cell. The constructs prepared utilized transcriptional initiation regions derived from genes preferentially expressed in a plant seed. Isolation of the cDNA sequences encoding the M. alpina Δ6 desaturase (SEQ ID NO:17 and SEQ ID NO:18) and M. alpina Δ12 desaturase (SEQ ID NO:19 and SEQ ID NO:20) are described in PCT Publications WO 98/46763 and WO 98/46764, the entireties of which are incorporated herein by reference.

For seed-specific expression, the Ma524 coding region was cut out of pCGN5535 as an XhoI fragment and inserted into the SalI site of the napin expression cassette, pCGN3223, to create pCGN5536. The NotI fragment of pCGN5536 containing the napin 5' regulatory region, the Ma524 coding region, and the napin 3' regulatory region was inserted into the NotI site of pCGN1557 to create pCGN5538.

The 5542 cDNA, encoding the *M. alpina* Δ12 desaturase, was modified by PCR to introduce cloning sites using the following primers:

Ma648PCR-for (SEQ ID NO:21)
  5'-CUACUACUACUAGGATCCATGGCACCTCCC AACACT

Ma648PCR-for (SEQ ID NO:22)
  5'-CAUCAUCAUCAUGGTACCTCGAGTTACTTC TTGAAAAAGAC

These primers allowed the amplification of the entire coding region and added a BamHI site to the 5' end and KpnI and XhoI sites to the 3' end. The PCR product was subcloned into pAMP1 (Gibco-BRL, Gaithersburg, Md.) using the CloneAmp system (Gibco-BRL) to create pCGN5540, and the Δ12 desaturase sequence was verified by sequencing of both strands.

A seed preferential expression construct was prepared for the Δ12 desaturase cDNA sequence. The Ma648 coding region was cut out of pCGN5540 as a BamHI/XhoI fragment and inserted between the BglII and XhoI sites of the napin expression cassette, pCGN3223 (described in U.S. Pat. No. 5,639,790), to create pCGN5542.

In order to express the *M. alpina* Δ6 and Δ12 desaturase sequences from the same T-DNA, the following construct for seed-preferential expression was prepared.

The NotI fragment of pCGN5536 containing the napin 5' transcriptional initiation region, the Ma524 coding region, and the napin 3' transcriptional termination region was inserted into the NotI site of pCGN5542 to create pCGN5544. The expression cassettes were oriented in such a way that the direction of transcription from Ma524 and Ma648 and the nptII marker is the same.

For seed-specific expression, the Ma524 coding region was cut out of pCGN5535 as an XhoI fragment and inserted into the SalI site of the napin expression cassette, pCGN3223, to create pCGN5536. The NotI fragment of pCGN5536 containing the napin 5 regulatory region, the Ma524 coding region, and the napin 3' regulatory region was inserted into the NotI site of pCGN1557 to create pCGN5538. pCGN5538 was introduced into *Brassica napus* cv.LP004 via Agrobacterium mediated transformation.

Maturing T2 seeds were collected from 6 independent transformation events in the greenhouse. The fatty acid composition of single seeds was analyzed by GC. Table 5 shows the results of control LP004 seeds and six 5538 lines. All of the 5538 lines except #8 produced seeds containing GLA. Presence of GLA segregated in these seeds as is expected for the T2 selfed seed population. In addition to GLA, the *M. alpina* Δ6 desaturase is capable of producing 18:4 (stearidonic) and another fatty acid: Δ6,9-18:2.

TABLE 5

Fatty Acid Analysis of Seeds from Ma524 Transgenic Brassica Plants

| SPL # | | 16:0 % | 16:1 % | 18:0 % | 18:1 % | 6,9 18:2 % | 18:2 % | 18:3ga % | 18:3 % | 18:4 % | 20:1 % | 22:0 % | 22:1 % | 24:0 % | 24:1 % |
|---|---|---|---|---|---|---|---|---|---|---|---|---|---|---|---|
| LP004 | -1 | 4.33 | 0.21 | 3.78 | 72.49 | 0 | 13.97 | 0 | 1.7 | 0 | 1.34 | 0.71 | 0.02 | 0.58 | 0.27 |
| | -2 | 4.01 | 0.16 | 3.09 | 73.59 | 0 | 14.36 | 0.01 | 1.4 | 0 | 1.43 | 0.66 | 0.02 | 0.5 | 0.2 |
| | -3 | 4.12 | 0.19 | 3.56 | 70.25 | 0 | 17.28 | 0 | 1.57 | 0 | 1.28 | 0.5 | 0.02 | 0.39 | 0.2 |
| | -4 | 4.22 | 0.2 | 2.7 | 70.25 | 0 | 17.86 | 0 | 1.61 | 0 | 1.31 | 0.53 | 0.02 | 0.4 | 0.24 |
| | -5 | 4.02 | 0.16 | 3.41 | 72.91 | 0 | 14.45 | 0.01 | 1.45 | 0 | 1.37 | 0.7 | 0.02 | 0.51 | 0.26 |
| | -6 | 4.22 | 0.18 | 3.23 | 71.47 | 0 | 15.92 | 0.01 | 1.52 | 0 | 1.32 | 0.69 | 0.02 | 0.51 | 0.27 |
| | -7 | 4.1 | 0.16 | 3.47 | 72.06 | 0 | 15.23 | 0 | 1.52 | 0 | 1.32 | 0.63 | 0.03 | 0.49 | 0.23 |
| | -9 | 4.01 | 0.17 | 3.71 | 72.98 | 0 | 13.97 | 0.01 | 1.41 | 0 | 1.45 | 0.74 | 0.03 | 0.58 | 0.23 |
| | -10 | 4.04 | 0.16 | 3.57 | 70.03 | 0 | 17.46 | 0 | 1.5 | 0 | 1.33 | 0.61 | 0.03 | 0.36 | 0.24 |
| 5538-1 | -1 | 4.61 | 0.2 | 3.48 | 68.12 | 1.37 | 10.68 | 7.48 | 1.04 | 0.33 | 1.19 | 0.49 | 0.02 | 0.33 | 0.13 |
| | -2 | 4.61 | 0.22 | 3.46 | 68.84 | 1.36 | 10.28 | 7.04 | 1.01 | 0.31 | 1.15 | 0.48 | 0.02 | 0.39 | 0 |
| | -3 | 4.78 | 0.24 | 3.24 | 65.86 | 0 | 21.36 | 0 | 1.49 | 0 | 1.08 | 0.46 | 0.02 | 0.38 | 0.22 |
| | -4 | 4.84 | 0.3 | 3.89 | 67.64 | 1.67 | 9.9 | 6.97 | 1.02 | 0.36 | 1.14 | 0.53 | 0.02 | 0.5 | 0.18 |
| | -5 | 4.64 | 0.2 | 3.58 | 64.5 | 3.61 | 8.85 | 10.14 | 0.95 | 0.48 | 1.19 | 0.47 | 0.01 | 0.33 | 0.12 |
| | -6 | 4.91 | 0.27 | 3.44 | 66.51 | 1.48 | 11.14 | 7.74 | 1.15 | 0.33 | 1.08 | 0.49 | 0.02 | 0.34 | 0.13 |
| | -7 | 4.87 | 0.22 | 3.24 | 65.78 | 1.27 | 11.92 | 8.38 | 1.2 | 0 | 1.12 | 0.47 | 0.02 | 0.37 | 0.16 |
| | -8 | 4.59 | 0.22 | 3.4 | 70.77 | 0 | 16.71 | 0 | 1.35 | 0 | 1.14 | 0.48 | 0.02 | 0.39 | 0.15 |
| | -9 | 4.63 | 0.23 | 3.51 | 69.66 | 2.01 | 8.77 | 7.24 | 0.97 | 0 | 1.18 | 0.52 | 0.02 | 0.3 | 0.11 |
| | -10 | 4.56 | 0.19 | 3.55 | 70.68 | 0 | 16.89 | 0 | 1.37 | 0 | 1.22 | 0.54 | 0.02 | 0.22 | 0.03 |
| 5538-3 | -1 | 4.74 | 0.21 | 3.43 | 67.52 | 1.29 | 10.91 | 7.77 | 1.03 | 0.28 | 1.11 | 0.5 | 0.02 | 0.35 | 0.14 |
| | -2 | 4.72 | 0.21 | 3.24 | 67.42 | 1.63 | 10.37 | 8.4 | 0.99 | 0 | 1.12 | 0.49 | 0.02 | 0.36 | 0.15 |
| | -3 | 4.24 | 0.21 | 3.52 | 71.31 | 0 | 16.53 | 0 | 1.33 | 0 | 1.12 | 0.45 | 0.02 | 0.4 | 0.14 |
| | -4 | 4.64 | 0.21 | 3.45 | 67.92 | 1.65 | 9.91 | 7.97 | 0.91 | 0.33 | 1.14 | 0.47 | 0.02 | 0.37 | 0.14 |
| | -5 | 4.91 | 0.25 | 3.31 | 67.19 | 0 | 19.92 | 0.01 | 1.39 | 0 | 1.05 | 0.48 | 0.02 | 0.37 | 0.14 |
| | -6 | 4.67 | 0.21 | 3.25 | 67.07 | 1.23 | 11.32 | 8.35 | 0.99 | 0 | 1.16 | 0.47 | 0.02 | 0.33 | 0.16 |
| | -7 | 4.53 | 0.19 | 2.94 | 64.8 | 4.94 | 8.45 | 9.95 | 0.93 | 0.44 | 1.13 | 0.37 | 0.01 | 0.27 | 0.12 |
| | -8 | 4.66 | 0.22 | 3.68 | 67.33 | 0.71 | 12 | 6.99 | 1.1 | 0.24 | 1.18 | 0.48 | 0.03 | 0.36 | 0.17 |
| | -9 | 4.65 | 0.24 | 3.11 | 67.42 | 0.64 | 12.71 | 6.93 | 1.16 | 0.25 | 1.08 | 0.45 | 0.02 | 0.32 | 0.17 |
| | -10 | 4.88 | 0.27 | 3.33 | 65.75 | 0.86 | 12.89 | 7.7 | 1.1 | 0.24 | 1.08 | 0.46 | 0.01 | 0.34 | 0.16 |
| 5538-4 | -1 | 4.65 | 0.24 | 3.8 | 62.41 | 0 | 24.68 | 0 | 1.6 | 0.01 | 0.99 | 0.45 | 0.02 | 0.33 | 0.13 |
| | -2 | 5.37 | 0.31 | 3 | 57.98 | 0.38 | 18.04 | 10.5 | 1.41 | 0 | 0.99 | 0.48 | 0.02 | 0.3 | 0.19 |
| | -3 | 4.61 | 0.22 | 3.07 | 63.62 | 0.3 | 16.46 | 7.67 | 1.2 | 0 | 1.18 | 0.45 | 0.02 | 0.29 | 0.14 |
| | -4 | 4.39 | 0.19 | 2.93 | 65.97 | 0 | 22.36 | 0 | 1.45 | 0 | 1.17 | 0.41 | 0.03 | 0.32 | 0.15 |
| | -5 | 5.22 | 0.29 | 3.85 | 62.1 | 2.35 | 10.25 | 11.39 | 0.93 | 0.41 | 1.04 | 0.6 | 0.02 | 0.47 | 0.17 |
| | -6 | 4.66 | 0.18 | 2.85 | 66.79 | 0.5 | 13.03 | 7.66 | 0.97 | 0.22 | 1.28 | 0.42 | 0.02 | 0.31 | 0.14 |
| | -7 | 4.85 | 0.26 | 3.03 | 57.43 | 0.26 | 28.04 | 0.01 | 2.59 | 0.01 | 1.13 | 0.56 | 0.02 | 0.4 | 0.23 |
| | -8 | 5.43 | 0.28 | 2.94 | 54.8 | 1.84 | 13.79 | 15.67 | 1.36 | 0.53 | 1.1 | 0.55 | 0.02 | 0.35 | 0.19 |
| | -9 | 4.88 | 0.24 | 3.32 | 62.3 | 0.58 | 14.86 | 9.04 | 1.34 | 0.29 | 1.13 | 0.52 | 0.02 | 0.37 | 0.19 |
| | -10 | 4.53 | 0.2 | 2.73 | 64.2 | 0.07 | 24.15 | 0 | 1.52 | 0 | 1.09 | 0.39 | 0.02 | 0.27 | 0.17 |
| 5538-5 | -1 | 4.5 | 0.15 | 3.35 | 66.71 | 0.88 | 11.7 | 8.38 | 1.04 | 0.3 | 1.24 | 0.49 | 0.02 | 0.29 | 0.17 |
| | -2 | 4.77 | 0.23 | 3.06 | 62.67 | 0.68 | 15.2 | 8.8 | 1.31 | 0.28 | 1.15 | 0.46 | 0.02 | 0.3 | 0.19 |

TABLE 5-continued

Fatty Acid Analysis of Seeds from Ma524 Transgenic Brassica Plants

| SPL # | 16:0 % | 16:1 % | 18:0 % | 18:1 % | 6,9 18:2 % | 18:2 % | 18:3ga % | 18:3 % | 18:4 % | 20:1 % | 22:0 % | 22:1 % | 24:0 % | 24:1 % |
|---|---|---|---|---|---|---|---|---|---|---|---|---|---|---|
| 3 | 4.59 | 0.22 | 3.61 | 64.33 | 2.29 | 9.95 | 10.57 | 1.01 | 0.45 | 1.21 | 0.48 | 0.02 | 0.26 | 0.16 |
| -4 | 4.86 | 0.26 | 3.4 | 67.69 | 0.65 | 12.24 | 6.61 | 1.09 | 0.23 | 1.07 | 0.45 | 0.02 | 0.32 | 0.14 |
| -5 | 4.49 | 0.21 | 3.3 | 69.25 | 0.04 | 16.51 | 2.18 | 1.2 | 0 | 1.11 | 0.44 | 0.02 | 0.33 | 0.16 |
| -6 | 4.5 | 0.21 | 3.47 | 70.48 | 0.08 | 14.9 | 2.19 | 1.22 | 0 | 1.13 | 0.49 | 0.02 | 0.33 | 0.16 |
| -7 | 4.39 | 0.21 | 3.44 | 67.59 | 2.38 | 9.24 | 8.98 | 0.89 | 0 | 1.18 | 0.44 | 0.02 | 0.28 | 0.14 |
| -8 | 4.52 | 0.22 | 3.17 | 68.33 | 0.01 | 18.91 | 0.73 | 1.32 | 0.01 | 1.08 | 0.45 | 0.02 | 0.29 | 0.17 |
| -9 | 4.68 | 0.2 | 3.05 | 64.03 | 1.93 | 11.03 | 11.41 | 1.02 | 0.01 | 1.15 | 0.39 | 0.02 | 0.21 | 0.15 |
| -10 | 4.57 | 0.2 | 3.1 | 67.21 | 0.61 | 12.62 | 7.68 | 1.07 | 0.25 | 1.14 | 0.43 | 0.02 | 0.25 | 0.15 |
| 5538-8-1 | 4.95 | 0.26 | 3.14 | 64.04 | 0 | 23.38 | 0 | 1.54 | 0 | 0.99 | 0.42 | 0.02 | 0.38 | 0.17 |
| -2 | 4.91 | 0.26 | 3.71 | 62.33 | 0 | 23.97 | 0 | 1.77 | 0 | 0.95 | 0.53 | 0.02 | 0.42 | 0.19 |
| -3 | 4.73 | 0.25 | 4.04 | 63.83 | 0 | 22.36 | 0.01 | 1.73 | 0 | 1.05 | 0.55 | 0.02 | 0.45 | 0.16 |
| -4 | 5.1 | 0.35 | 3.8 | 60.45 | 0 | 24.45 | 0.01 | 2.13 | 0 | 1.07 | 0.65 | 0.03 | 0.53 | 0.24 |
| -5 | 4.98 | 0.3 | 3.91 | 62.48 | 0 | 23.44 | 0 | 1.77 | 0 | 1.01 | 0.51 | 0.01 | 0.43 | 0.21 |
| -6 | 4.62 | 0.21 | 3.99 | 66.14 | 0 | 20.38 | 0 | 1.48 | 0 | 1.15 | 0.53 | 0.02 | 0.48 | 0.19 |
| -7 | 4.64 | 0.22 | 3.55 | 64.6 | 0 | 22.65 | 0 | 1.38 | 0 | 1.09 | 0.45 | 0.02 | 0.41 | 0.19 |
| -8 | 5.65 | 0.38 | 3.18 | 56.6 | 0 | 30.83 | 0.02 | 0.02 | 0 | 0.98 | 0.55 | 0.03 | 0.39 | 0.26 |
| -9 | 8.53 | 0.63 | 6.9 | 51.76 | 0 | 26.01 | 0 | 0.01 | 0 | 1.41 | 1.21 | 0.07 | 0.96 | 0.33 |
| -10 | 5.52 | 0.4 | 3.97 | 57.92 | 0 | 28.95 | 0 | 0.02 | 0 | 0.95 | 0.52 | 0.02 | 0.41 | 0.16 |
| 5538-10-1 | 4.44 | 0.19 | 3.5 | 68.42 | 0 | 19.51 | 0 | 1.32 | 0 | 1.14 | 0.45 | 0.02 | 0.31 | 0.16 |
| -2 | 4.57 | 0.21 | 3.07 | 66.08 | 0 | 21.99 | 0.01 | 1.36 | 0 | 1.12 | 0.41 | 0.02 | 0.31 | 0.16 |
| -3 | 4.63 | 0.21 | 3.48 | 67.43 | 0 | 20.27 | 0.01 | 1.32 | 0 | 1.12 | 0.46 | 0.02 | 0.21 | 0.08 |
| 4 | 4.69 | 0.19 | 3.22 | 64.62 | 0 | 23.16 | 0 | 1.35 | 0 | 1.08 | 0.46 | 0.02 | 0.33 | 0.2 |
| -5 | 4.58 | 0.2 | 3.4 | 68.75 | 0 | 20.17 | 0.01 | 0.02 | 0 | 1.1 | 0.45 | 0.02 | 0.34 | 0.17 |
| -8 | 4.55 | 0.21 | 0 | 73.55 | 0.05 | 14.91 | 2.76 | 1.21 | 0.07 | 1.24 | 0.51 | 0.02 | 0.19 | 0 |
| -9 | 4.58 | 0.21 | 3.28 | 66.19 | 0 | 21.55 | 0 | 1.35 | 0 | 1.12 | 0.43 | 0.02 | 0.33 | 0.16 |
| -10 | 4.52 | 0.2 | 3.4 | 68.37 | 0 | 19.33 | 0.01 | 1.3 | 0 | 1.13 | 0.46 | 0.02 | 0.35 | 0.18 |

Crosses were made between transgenic Brassica 5544 lines producing GLA and standard non-transformed canola varieties. Crosses between 5544 lines with Quantum, Eagle, and Ebony were conducted.

F1 half seeds were analyzed for SDA content and selected plants were grown and allowed to self-pollinate to produce F2 seeds. GC-FAME analysis of both single seed and half-seed samples from such crosses revealed accumulation of significant levels of SDA (Table 6). Half-seed analysis of 5544-LP108-6-16 with canola variety Eagle yielded a level of approximately 6.3% SDA. Analysis of F2 seed from a cross of 5544-LP108-12-1 with the canola variety Ebony produced levels of SDA as high as about 7.4% SDA.

transgenic canola. Table 4 in that example showed examples of single seed analyses from 6 independent transgenic events. Significant amounts of GLA were produced, in addition to the Δ-6,9 18:2 fatty acid.

A total of 29 independent pCGN5538-transformed transgenic plants of the low-linolenic LP004 cultivar were regenerated and grown in the greenhouse. Table 7 shows the fatty acid composition of 20-seed pools of T2 seed from each event. Seven of the lines contained more than 2% of the Δ-6,9 18:2 in the seed pools. To identify and select plants with high amounts of Δ-6,9 18:2 to be taken on to subsequent generations, half-seed analysis was done. Seeds were

TABLE 6

| STRAIN ID | 16:0 | 16:1 | 18:0 | 18:1 | 18:2 C69 | 18:2 C912 | 18:3 C6912 | 18:3 C91215 | 18:4 | 20:0 | 20:1 | 20:2 | 22:0 |
|---|---|---|---|---|---|---|---|---|---|---|---|---|---|
| (SP30035-46 x 5544-LP30108-6-16) | 6.34 | 0.84 | 1.9 | 4.7 | 0 | 14.81 | 56.73 | 3.78 | 6.29 | 2.12 | 0.66 | 0.59 | 1.04 |
| (SP30035-46 x 5544-LP30108-6-16) | 10.18 | 1.43 | 4.23 | 4.34 | 0 | 15.96 | 48.78 | 3.79 | 5.51 | 2.65 | 0.72 | 0.77 | 1.32 |
| (SP30035-46 x 5544-LP30108-6-16) | 4.81 | 0.45 | 2.53 | 12.2 | 0 | 21.61 | 46.74 | 4.83 | 4.11 | 0.98 | 0.79 | 0.4 | 0.43 |
| (SP30035-46 x 5544-LP30108-6-16) | 4.74 | 0.48 | 3.33 | 16.06 | 0 | 20.68 | 43.02 | 4.82 | 3.73 | 1.25 | 0.7 | 0.33 | 0.75 |
| (SP30035-46 x 5544-LP30108-6-16) | 6.02 | 0.53 | 1.25 | 17.29 | 0 | 27.34 | 33.97 | 7.52 | 3.41 | 0.85 | 0.77 | 0.27 | 0.59 |
| (SP30035-46 x 5544-LP30108-6-16) | 3.68 | 0.13 | 1.99 | 19.75 | 0.09 | 22.75 | 39.98 | 5.76 | 3.41 | 0.8 | 0.87 | 0.27 | 0.44 |
| (SP30052-7 x 5544-LP30108-12-1) | 8.92 | 0.96 | 1.64 | 14.61 | 0 | 18.69 | 36.98 | 7.44 | 7.43 | 1.01 | 0.49 | 0.49 | 0.95 |
| (SP30052-7 x 5544-LP30108-12-1) | 9.02 | 0.89 | 1.88 | 10.69 | 0 | 16.73 | 43.39 | 6.8 | 6.76 | 1.05 | 0.57 | 0.75 | 1.07 |
| (SP30052-7 x 5544-LP30108-12-1) | 7.76 | 0.59 | 1.86 | 8.15 | 0 | 16.04 | 52.24 | 4.65 | 5.3 | 1.04 | 0.59 | 0.69 | 0.83 |
| (SP30052-7 x 5544-LP30108-12-1) | 9.21 | 0.87 | 2.23 | 17.44 | 0 | 18.77 | 36.87 | 6.79 | 5.05 | 0.84 | 0.64 | 0.31 | 0.71 |
| (SP30052-7 x 5544-LP30108-12-1) | 5.76 | 0.31 | 1.6 | 20.38 | 0 | 24.36 | 29.94 | 10.9 | 4.41 | 0.69 | 0.78 | 0.23 | 0.48 |
| (SP30052-7 x 5544-LP30108-12-1) | 4.03 | 0.22 | 1.3 | 16.87 | 0 | 19.3 | 46.67 | 5.33 | 4.17 | 0.53 | 0.75 | 0.35 | 0.37 |
| (SP30052-7 x 5544-LP30108-12-1) | 4.66 | 0.29 | 4.47 | 18.09 | 0.05 | 19.07 | 41.92 | 5.06 | 3.47 | 1.13 | 0.73 | 0.35 | 0.57 |
| (SP30052-7 x 5544-LP30108-12-1) | 4.91 | 0.26 | 3.13 | 18.16 | 0 | 18.53 | 43.99 | 4.64 | 3.43 | 1.01 | 0.79 | 0.37 | 0.66 |

Example 6

Production of Δ6,9 18:2 in Canola Oil

Example 5 described construction of pCGN5538 designed to express the *M. alpina* Δ6 desaturase in seeds of germinated overnight in the dark at 30 degrees on water-soaked filter paper. The outer cotyledon was excised for GC analysis and the rest of the seedling was planted in soil. Based on results of fatty acid analysis, selected T2 plants were grown in the greenhouse to produce T3 seed. The-selection cycle was repeated; pools of T3 seed were analyzed for Δ-6,9 18:2, T3 half-seeds were dissected and analyzed, and selected T3 plants were grown in the greenhouse to produce T4 seed. Pools of T4 seed were analyzed for fatty acid composition. Table 6 summarizes the results of this process for lines derived from one of the original To maximize the amount of Δ-6,9 18:2 that could be produced, the pCGN5538 construct could be introduced into a high oleic acid variety of canola either by transformation or crossing. A high-oleic variety could be obtained by mutation, co-suppression, or antisense suppression of the Δ12 and Δ15 desaturases or other necessary co-factors.

TABLE 7

Fatty Acid Compositions of 20-seed Pools of pCGN5538 T2 Seeds

| SPL # | 5538-LP004 event | 12:0 % | 14:0 % | 16:0 % | 16:1 % | 18:0 % | 18:1 % | Δ6,9 18:2 % | 18:2 % | Δ6,9,12 18:3 % | Δ9,12,15 18:3 % | 18:4 % | 20:0 % | 20:1 % | 20:2 % | 22:0 % | 22:2 % |
|---|---|---|---|---|---|---|---|---|---|---|---|---|---|---|---|---|---|
| | 31 | 0.02 | 0.06 | 4.07 | 0.07 | 0 | 59.4 | 5.4 | 10.07 | 15.93 | 1.2 | 0.6 | 0.98 | 1.16 | 0.0 | 0.44 | 0.03 |
| | 29 | 0.01 | 0.05 | 3.81 | 0.14 | 0 | 60.7 | 4.53 | 10.9 | 14.77 | 1.03 | 0.55 | 1.09 | 1.26 | 0.0 | 0.46 | 0.02 |
| | 19 | 0.02 | 0.07 | 4.27 | 0.13 | 0 | 62.9 | 4.17 | 10.03 | 13.14 | 1.02 | 0.59 | 1.18 | 1.25 | 0.0 | 0.53 | 0.02 |
| | 14 | 0 | 0 | 5.29 | 0.24 | 3.8 | 49.1 | 1.02 | 23.44 | 11.21 | 2.26 | 0.34 | 1.45 | 0.93 | 0.0 | 0.76 | 0 |
| | 22 | 0.02 | 0.05 | 3.87 | 0.09 | 0 | 64.1 | 2.59 | 12.57 | 11.18 | 1.27 | 0.6 | 1.18 | 1.08 | 0.1 | 0.56 | 0 |
| | 9 | 0.01 | 0.06 | 4.57 | 0.16 | 0 | 62.9 | 3.4 | 12.05 | 11.15 | 1.27 | 0.6 | 1.28 | 1.18 | 0.0 | 0.56 | 0.03 |
| | 25 | 0.01 | 0.06 | 4.17 | 0.14 | 0 | 62.4 | 2.49 | 14.42 | 11.03 | 1.2 | 0.46 | 1.18 | 1.15 | 0.0 | 0.53 | 0.01 |
| | 15 | 0.01 | 0.05 | 3.94 | 0.11 | 0 | 65.2 | 2.08 | 12.77 | 10.9 | 1.04 | 0.43 | 1.1 | 1.24 | 0.0 | 0.48 | 0.01 |
| | 18 | 0 | 0.06 | 5.34 | 0.29 | 0 | 58.4 | 1.42 | 18.19 | 10.53 | 1.8 | 0.49 | 1.2 | 1 | 0.0 | 0.58 | 0.02 |
| | 20 | 0.01 | 0.04 | 3.95 | 0.1 | 0 | 65.6 | 1.31 | 13.83 | 10.22 | 1.09 | 0.39 | 1.06 | 1.3 | 0.0 | 0.46 | 0.01 |
| | 7 | 0.02 | 0.07 | 4.04 | 0.11 | 0 | 62.1 | 0.92 | 18.12 | 8.72 | 1.77 | 0.35 | 1.26 | 1.19 | 0.0 | 0.58 | 0 |
| | 11 | 0.01 | 0.06 | 4.23 | 0.17 | 0 | 62.9 | 1.6 | 17.19 | 8.58 | 1.48 | 0.38 | 1.16 | 1.03 | 0.0 | 0.49 | 0.01 |
| | 27 | 0.02 | 0 | 3.99 | 0.14 | 0 | 65.3 | 0.64 | 17.85 | 7.89 | 1.36 | 0.31 | 1.08 | 1.21 | 0.0 | 0 | 0 |
| | 2 | 0.01 | 0.05 | 4.02 | 0.14 | 0 | 66.4 | 1.2 | 15.74 | 7.58 | 1.22 | 0.32 | 1.06 | 1.19 | 0.0 | 0.45 | 0 |
| | 28 | 0.01 | 0.04 | 3.77 | 0.11 | 0 | 67.5 | 0.79 | 15.56 | 7.58 | 1.12 | 0.28 | 0.97 | 1.23 | 0.0 | 0.44 | 0 |
| | 3 | 0.01 | 0.05 | 3.96 | 0.12 | 0 | 68.5 | 1.81 | 13.23 | 7.44 | 1.1 | 0.35 | 1.12 | 1.21 | 0.0 | 0.46 | 0.01 |
| | 21 | 0.01 | 0.05 | 3.74 | 0.1 | 0 | 66.9 | 1.16 | 15.9 | 6.97 | 1.35 | 0.28 | 1.15 | 1.27 | 0.0 | 0.52 | 0 |
| | 5 | 0.01 | 0.04 | 3.81 | 0.12 | 0 | 69.1 | 0.74 | 14.58 | 6.95 | 1.14 | 0.28 | 1.06 | 1.18 | 0.0 | 0.45 | 0 |
| | 6 | 0 | 0 | 2.84 | 0 | 3.06 | 62.5 | 1.55 | 18.44 | 6.94 | 1.21 | 0.39 | 1.04 | 1.33 | 0.1 | 0 | 0 |
| | 4 | 0.01 | 0.05 | 3.88 | 0.11 | 0 | 66.9 | 0.64 | 16.21 | 6.89 | 1.52 | 0.31 | 1.09 | 1.21 | 0.0 | 0.5 | 0 |
| | 30 | 0.01 | 0.04 | 3.89 | 0.12 | 0 | 68.6 | 0.72 | 15.58 | 6.47 | 1.17 | 0.23 | 1.03 | 1.07 | 0.0 | 0.46 | 0 |
| | 16 | 0.02 | 0.05 | 3.75 | 0.13 | 0 | 70.4 | 0.91 | 13.56 | 6.39 | 1.13 | 0.28 | 1.04 | 1.2 | 0.0 | 0.44 | 0.01 |
| | 26 | 0.01 | 0 | 3.77 | 0.12 | 0 | 67.6 | 0 | 21.08 | 3.61 | 1.37 | 0.13 | 0.96 | 1.16 | 0.0 | 0 | 0 |
| | 23 | 0 | 0 | 4.92 | 0.22 | 0 | 65.2 | 0 | 22.23 | 3 | 1.79 | 0.11 | 1.28 | 1.11 | 0.0 | 0 | 0 |
| | 24 | 0.01 | 0 | 3.84 | 0.13 | 0 | 68.4 | 0.36 | 21 | 2.09 | 1.53 | 0.08 | 1.06 | 1.27 | 0.0 | 0 | 0 |
| | 10 | 0.01 | 0 | 3.74 | 0.11 | 0 | 70.4 | 0 | 20.82 | 0.65 | 1.3 | 0.03 | 1.05 | 1.18 | 0.0 | 0.46 | 0 |
| | 12 | 0.01 | 0 | 3.83 | 0.12 | 0 | 69.9 | 0 | 21.61 | 0.34 | 1.34 | 0 | 1.06 | 1.12 | 0.0 | 0.47 | 0 |
| | 17 | 0.01 | 0 | 0 | 0.13 | 0 | 72.6 | 0 | 23.03 | 0.24 | 1.51 | 0 | 1.18 | 1.21 | 0.0 | 0 | 0 |
| | 8 | 0.01 | 0 | 4.54 | 0.2 | 0 | 64.9 | 0 | 25.65 | 0.22 | 1.94 | 0 | 1.38 | 1.01 | 0.0 | 0 | 0 |
| | 13 | 0.01 | 0 | 3.99 | 0.16 | 0 | 65.8 | 0 | 25.9 | 0 | 1.58 | 0 | 1.17 | 1.16 | 0.0 | 0 | 0 |
| | LP004 control | 0.01 | 0.04 | 3.46 | 0.09 | 0 | 69.9 | 0 | 21.95 | 0 | 1.37 | 0.01 | 0.9 | 1.25 | 0.0 | 0.42 | 0 |

| STRAIN IDΔ | T2 Pool Δ6,9 18:2 | GLA | T3 Pool Δ6,9 18:2 | GLA | T3 selection Δ6,9 18:2 | GLA | T4 Pool Δ6,9 18:2 | Δ6,9,12 18:3 |
|---|---|---|---|---|---|---|---|---|
| 5538-LP004-25 | 2.49 | 11.03 | | | | | | |
| 5538-LP004-25-3 | | | 9.1 | 11.92 | | | | |
| 5538-LP004-25-3-31 | | | | | 13.61 | 7.82 | 11.02 | 9.41 |
| 5538-LP004-25-3-30 | | | | | 6.51 | 7.93 | 10.27 | 8.7 |
| 5538-LP004-25-3-29 | | | | | 13.35 | 11.23 | 9.42 | 10.5 |
| 5538-LP004-25-3-28 | | | | | 9.92 | 24.1 | 9.37 | 10.19 |
| 5538-LP004-25-3-25 | | | | | 5.3 | 30.34 | 7.95 | 11.34 |
| 5538-LP004-25-2 | | | 3.87 | 11.08 | | | | |
| 5538-LP004-25-2-29 | | | | | 13.63 | 7.41 | 9.6 | 11.07 |
| 5538-LP004-25-2-27 | | | | | 5.02 | 22.04 | 6.95 | 9.61 |
| 5538-LP004-25-2-26 | | | | | 1.21 | 26.84 | 4.31 | 7.45 |
| 5538-LP004-25-2-25 | | | | | 5.83 | 34.16 | 8.77 | 11.58 |
| 5538-LP004-25-13 | | | 10.53 | 11.19 | | | | |
| 5538-LP004-25-13-27 | | | | | 14.65 | 11.46 | 7.86 | 10.49 |
| 5538-LP004-25-13-26 | | | | | 11.18 | 13.04 | 9.33 | 10.01 |
| 5538-LP004-25-13-25 | | | | | 4.18 | 36.78 | 7.2 | 12.22 |
| 5538-LP004-25-1 | | | 3.05 | 11.16 | | | | |
| 5538-LP004-25-1-41 | | | | | 0 | 0 | 0.01 | 0.04 |
| 5538-LP004-25-1-28 | | | | | 3.43 | 19.98 | 4.63 | 6.53 |
| 5538-LP004-25-1-27 | | | | | 5.52 | 20.13 | 8.35 | 11.21 |
| 5538-LP004-25-1-26 | | | | | 0.1 | 25.16 | 5.52 | 8.59 |
| 5538-LP004-25-1-25 | | | | | 6.5 | 31.83 | 9.85 | 10.88 | transgenic events, 5538-LP004-25. Levels of Δ-6,9 18:2 have thus been maintained through 3 generations.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for producing stearidonic acid in a plant seed, said method comprising:

growing a plant having integrated into its genome a first DNA construct comprising, in the 5' to 3' direction of transcription, a promoter functional in a plant seed cell, a DNA sequence encoding a delta-six desaturase, and a transcription termination region functional in a plant cell, and growing said plant under conditions whereby said delta-six desaturase is expressed.

2. The method according to claim 1 wherein said plant has a second construct integrated into its genome, wherein said second construct has in the 5' to 3' direction of transcription, a promoter functional in a plant seed cell, and a DNA sequence encoding a delta 12 desaturase.

3. The method according to claim 1 wherein said plant has a second construct integrated into its genome, wherein said second construct has in the 5' to 3' direction of transcription, a promoter functional in a plant seed cell, and a DNA sequence encoding a delta 15 desaturase.

4. The method of claim 1 wherein said desaturase encoding sequence is from the genus Mortierella.

5. The method according to claim 1, wherein said promoter is a napin promoter.

6. The method according to claim 1, wherein said promoter is from the soybean β-conglycinin 7S subunit transcription initiation region.

7. The method according to claim 1, wherein said method further comprises extracting oil from said plant seed.

8. The method of claim 7, wherein said oil comprises about 5 weight percent or greater stearidonic acid.

9. The method of claim 7, wherein said oil comprises about 10 weight percent or greater stearidonic acid.

10. The method of claim 7, wherein said oil comprises about 15 weight percent or greater stearidonic acid.

11. The method of claim 7, wherein said oil comprises about 20 weight percent or greater stearidonic acid.

12. The method of claim 7, wherein said oil comprises about 25 weight percent or greater stearidonic acid.

* * * * *